(12) United States Patent
Denis

(10) Patent No.: US 10,470,957 B1
(45) Date of Patent: Nov. 12, 2019

(54) POSITIONING DEVICE FOR BEAM RADIATION TREATMENT AND IMAGING

(71) Applicant: Carl Denis, Dewinton (CA)

(72) Inventor: Carl Denis, Dewinton (CA)

( * ) Notice: Subject to any disclaimer, the term of this patent is extended or adjusted under 35 U.S.C. 154(b) by 520 days.

(21) Appl. No.: 15/134,200

(22) Filed: Apr. 20, 2016

Related U.S. Application Data

(60) Provisional application No. 62/152,551, filed on Apr. 24, 2015.

(51) Int. Cl.
| | | |
|---|---|---|
| *A61G 7/07* | (2006.01) | |
| *A61G 7/015* | (2006.01) | |
| *A61B 6/04* | (2006.01) | |
| *A61G 13/12* | (2006.01) | |

(52) U.S. Cl.
CPC .............. *A61G 7/07* (2013.01); *A61B 6/0407* (2013.01); *A61B 6/0421* (2013.01); *A61G 7/015* (2013.01); *A61G 13/121* (2013.01)

(58) Field of Classification Search
CPC ....... A61B 6/04; A61B 6/0407; A61B 6/0492; A61B 6/0421; A61G 13/02; A61G 13/08; A61G 2210/50; A61G 7/00; A61G 7/002; A61G 7/015; A61G 7/018; A61G 7/07; A61G 7/075; A61G 7/0755; A61G 7/065
See application file for complete search history.

(56) References Cited

U.S. PATENT DOCUMENTS

| | | | | |
|---|---|---|---|---|
| 1,452,915 A | * | 4/1923 | Kennedy | A47C 20/022 297/423.46 |
| 3,565,419 A | * | 2/1971 | Allard | A61G 13/12 297/377 |
| 3,753,557 A | * | 8/1973 | Kelley | A61G 13/12 5/648 |
| 4,000,736 A | * | 1/1977 | Bruscemi | A47C 20/021 602/5 |
| 4,688,851 A | * | 8/1987 | Whiteford | A47C 7/14 297/313 |
| 5,316,370 A | * | 5/1994 | Newman | A61G 5/14 297/313 |
| 5,318,422 A | | 6/1994 | Erland | |
| 5,775,337 A | * | 7/1998 | Hauger | A61B 6/0421 128/869 |

(Continued)

FOREIGN PATENT DOCUMENTS

EP 2682550 A1 1/2014

OTHER PUBLICATIONS http://www.civco.com/ro/breast-positioning/breastboards/Thorawedge.htm; Thorawedge; Copyright 2015, CIVCO Medical Solutions; 1 Page.
http://www.civco.com/ro/breast-positioning/breastboards/cqual-breastboard-B1.htm; C-Qual Breastboard; Copyright 2015, CIVCO Medical Solutions; 2 Pages.

(Continued)

*Primary Examiner* — Nicholas F Polito
(74) *Attorney, Agent, or Firm* — Spencer Fane LLP; David A. Banko

(57) ABSTRACT

A system and method are disclosed for a patient positioning device for beam radiation therapy and radiological imaging. The system includes a base and a patient support surface coupled to the base, and the patient support surface includes a lower patient support hingedly coupled to the base and an upper support hingedly coupled to the lower patient support. The system also includes a substantially flat hinge that forms a continuous upper surface with an upper support surface of the lower patient support and the lower patient support.

22 Claims, 15 Drawing Sheets

(56) References Cited

U.S. PATENT DOCUMENTS

| | | | |
|---|---|---|---|
| 8,336,142 B1* | 12/2012 | See | A61G 13/1215 5/633 |
| 2003/0078144 A1* | 4/2003 | Gehrke | A47C 20/021 482/140 |
| 2012/0011653 A1* | 1/2012 | Coppens | A61B 6/00 5/601 |
| 2012/0138065 A1* | 6/2012 | Campagna | A61B 5/0555 128/845 |
| 2013/0061398 A1* | 3/2013 | Lim | A61G 7/015 5/616 |
| 2013/0145553 A1* | 6/2013 | Shih | A61G 7/015 5/624 |
| 2013/0278019 A1* | 10/2013 | Preisler | B60R 5/04 296/193.07 |
| 2015/0208990 A1* | 7/2015 | Stoutenburgh | A61B 6/0407 378/62 |
| 2016/0213337 A1* | 7/2016 | Coppens | A61N 5/10 |

OTHER PUBLICATIONS http://www.qfix.com/qfix-products/breast-and-torso.asp?CID=4&PLID=67; Access Supine Devices; Copyright 2016, Qfix; 3 Pages.

http://www.bionixrt.com/RT_PDFs/SELLSHEET_Max3.pdf; Max3 Plus Breast Board; Copyright 2013, Bionix Radiation Therapy; 2 Pages.

http://www.civco.com/ro/breast-positioning/breastboards/C-Qual-M-Breastboard.htm; C-Qual M Breastboard; Copyright 2015, CIVCO Medical Solutions; 2 Pages.

http://www.civco.com/ro/breast-positioning/breastboards/mt350-mt250-breastboards-MT350N.htm; MT-350 Breastboard; Copyright 2015, CIVCO Medical Solutions; 2 Pages.

http://www.civco.com/ro/breast-positioning/breastboards/posiboard2-breastboard-109030.htm; Posiboard-2 Breastboard; Copyright 2015, CIVCO Medical Solutions; 2 Pages.

http://www.qfix.com/qfix-products/breast-and-torso.asp?CID=4&PLID=17; QUEST; Copyright 2016, Qfix; 3 Pages.

\* cited by examiner

POSITIONING DEVICE FOR BEAM RADIATION TREATMENT AND IMAGING

CROSS-REFERENCE TO RELATED APPLICATIONS

The present disclosure is related to that disclosed in the U.S. Provisional Application No. 62/152,551, filed Apr. 24, 2015, entitled "Positioning Device for Beam Radiation Treatment and Imaging." U.S. Provisional Application No. 62/152,551 is assigned to the assignee of the present application. The subject matter disclosed in U.S. Provisional Application No. 62/152,551 is hereby incorporated by reference into the present disclosure as if fully set forth herein. The present invention hereby claims priority under 35 U.S.C. § 119(e) to U.S. Provisional Application No. 62/152,551.

TECHNICAL FIELD

The disclosure relates generally to a system and method for beam radiation therapy and radiological imaging, and more particularly to a flexible and secure patient-positioning device for radiation therapy and radiological imaging.

BACKGROUND

The trend in cancer treatment is moving toward higher doses of radiation over fewer treatments, advanced imaging techniques like cone beam computed tomography (CBCT), and increased beam angles and delivery techniques such as arching treatments. This trend, however, necessitates a corresponding increase in the accuracy of patient positioning, and increase in the optimization of device construction to reduce the attenuation of the beam or obstruction of the imaging issued in conjunction with beam therapy. Currently available patient-positioning devices have proven inadequate and their inability to accurately position patients has proven undesirable.

BRIEF DESCRIPTION OF THE DRAWINGS

A more complete understanding of the present invention may be derived by referring to the detailed description when considered in connection with the following illustrative figures. In the figures, like reference numbers refer to like elements or acts throughout the figures.

DETAILED DESCRIPTION

Figure 1:
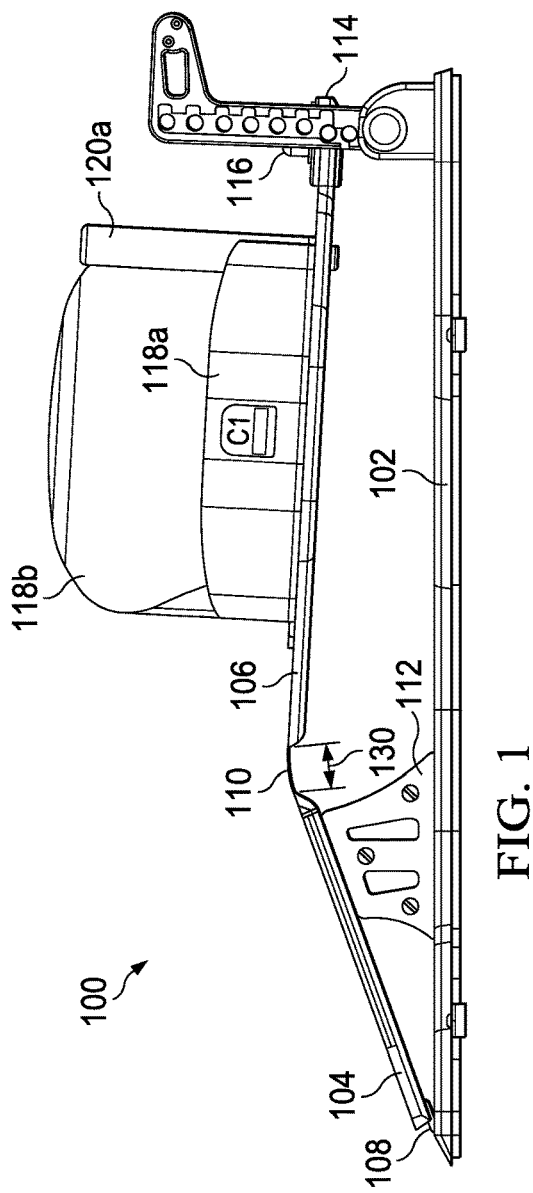
FIG. 1 illustrates a side view of an exemplary patient positioning device according to an embodiment.
Figure 1:
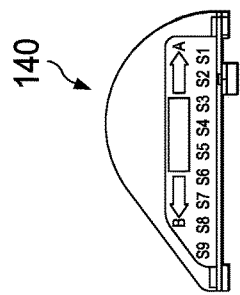

Systems and methods for patient positioning during radiation treatment and applications of the invention presented herein are described below in the drawings and detailed description of the invention. Unless specifically noted, it is intended that the words and phrases herein be given their plain, ordinary, and accustomed meaning to those of ordinary skill in the applicable arts.

In the following description, and for the purposes of explanation, numerous specific details are set forth in order to provide a thorough understanding of the various aspects of the invention. It will be understood, however, by those skilled in the relevant arts, that embodiments of the present invention may be practiced without these specific details. In other instances, known structures and devices are shown and/or discussed more generally in order to avoid obscuring the invention. In many cases, a description of the operation is sufficient to enable one of ordinary skill in the applicable art to implement the various forms of the invention. It should be appreciated that there are many different and alternative configurations, devices and technologies to which the disclosed inventions may be applied. The full scope of the present disclosure is not limited to the examples described below.

Embodiments of the following disclosure provide for a dual axis patient positioning device comprising an easily positionable and radio-translucent treatment couch overlay for radiological treatment and medical imaging, such as by a radiological therapy device. According to aspects of the disclosure, the patient positioning device comprises one or more features that provide for increased patient comfort and better patient positioning, which increases the efficacy of treatment and imaging. Embodiments of the current invention provide for an indexable and comfortable method to optimize a patient's chin and cranial position independently of breasts or chest in a sloped position. According to an aspect, patient positioning device provides for patient positions which are not available on conventional treatment couch overlays.

Conventional single-axis breast boards result in limited patient positioning options and make it cumbersome to reposition a patient. Embodiments of the current disclosure provide for increased patient positioning options by various adjustable modules and a dual-axis hinge design. According to a further aspect, patient positioning device provides for a couch overlay that may be adjustable by a single therapist with one hand and even for the largest patients. Embodiments also provide positioning attachments for a patient's neck, face, and arms that provide additional patient positioning options and increased patient stability.

According to a further aspect, the initial-angle positioning module and upper-angle positioning module provide enhanced stability and reduce or eliminate positional injuries to patients and therapists. Embodiments also provide for a lightweight design that can be quickly and securely adjusted and indexed to maximize treatment requirements and patient comfort. Nearly all adjustments may be made to the system with the patient in situ, thereby saving time and maximizing patient comfort and safety.

FIG. 1 illustrates a first view of the patient-positioning device 100 according to an embodiment. The patient positioning device 100 may comprise one or more of the following: base 102, lower patient support 104, upper patient support 106, initial-angle hinge 108, upper-angle hinge 110, initial-angle positioning module 112, upper-angle positioning module 114, upper-angle lock knob 116, arm-positioning bolsters 118a-118b, and arm-positioning hand grips 120a-120b.

Base 102 may be coupled to lower patient support 104 by initial-angle hinge 108. Lower patient support 104 may, in turn, be coupled to upper patient support 106 by upper-angle hinge 110. According to embodiments, the patient positioning device 100 is designed to support and distribute the weight of a patient on the lower patient support 104 and upper patient support 106. The base 102, lower patient support 104, and upper patient support 106 may be manufactured from carbon fiber and epoxy resin with a low density foam core.

Figure 8:
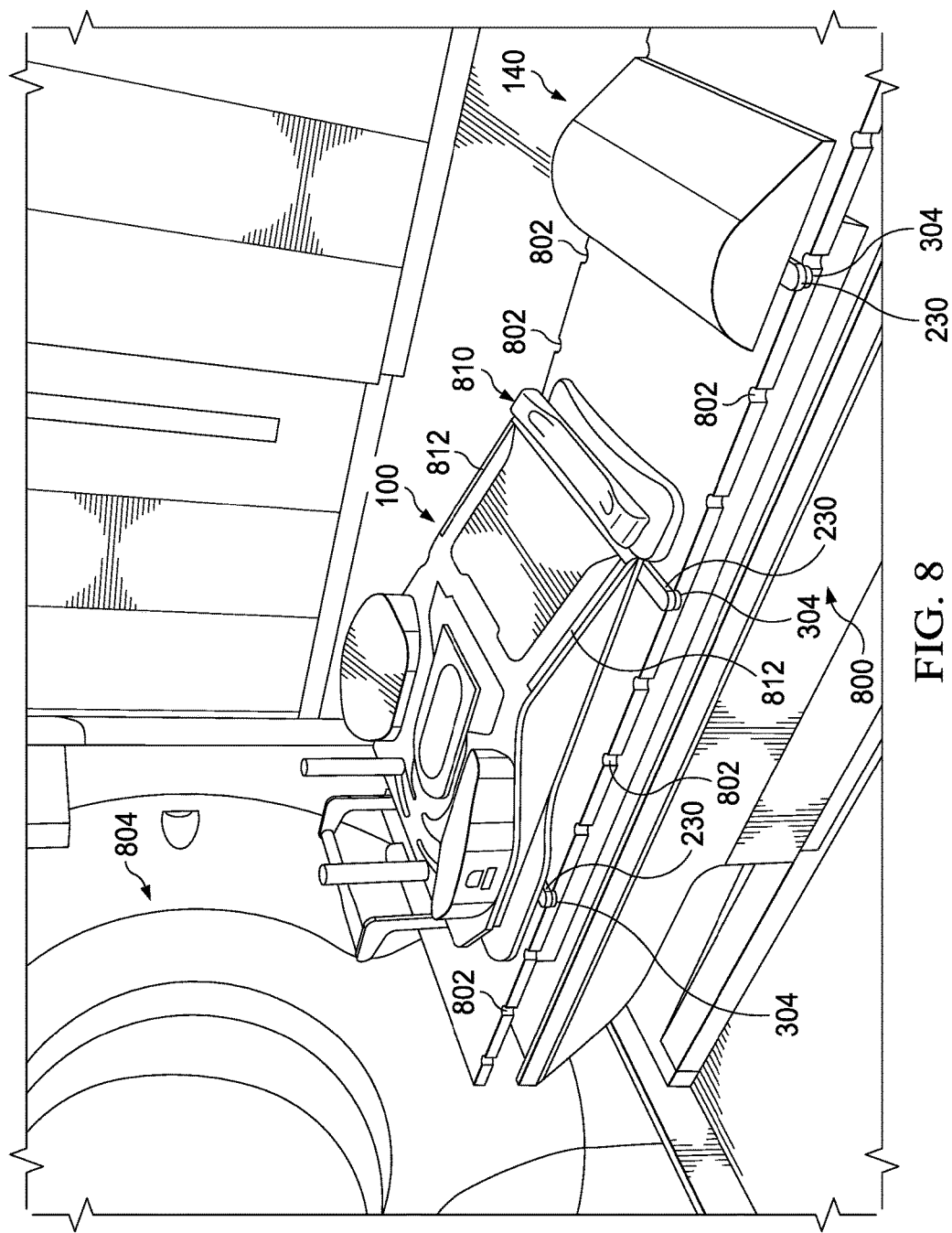
FIG. 8 illustrates an exemplary patient positioning device coupled to a treatment bed according to an embodiment.

Additionally, patient positioning device 100 may be used in conjunction with patient stop 140, which may provide additional support for positioning a patient for therapy or imaging. According to some embodiments, patient stop 140 provides a stopping support to prevent a patient from sliding down a treatment table or treatment couch 800 (FIG. 8). For example, some treatment tables may need to be inclined to provide for imaging or treatment of a patient. Patient stop 140 may couple to treatment couch 800 underneath the buttocks of a patient to prevent the patient from sliding down the inclined treatment couch 800, as will be discussed in more detail below.

Lower patient support 104 may couple with base 102 by initial-angle hinge 108. Initial-angle hinge 108 may comprise one or more hinged elements coupled with base 102 and lower patient support 104 that provide for lower patient support 104 to pivot around an axis parallel to base 102 so that lower patient support 104 may be lifted upward and away from base. According to embodiments, initial-angle hinge 108 may comprise any suitable mechanism for allowing lower patient support 104 to be raised away from base 102 to allow insertion of initial-angle positioning module 112, such as, for example a flat or butt hinge, spring-loaded hinge, ball-bearing hinge, strap hinge, or any other suitable positioning device. According to some embodiments, initial-angle hinge 108 may comprise a fiber-reinforced hinge, as described in connection with upper-angle hinge. Description of the initial-angle hinge 108 and initial-angle positioning module 112 will be described in more detail below.

Upper patient support 106 may couple to the lower patient support 104 by upper-angle hinge 110. Upper-angle hinge 110 may comprise an upper surface that is substantially continuous with the upper surfaces of lower patient support 104 and upper patient support 106. In this way, the upper surfaces of the lower patient support 104, upper-angle hinge 110, and lower patient support 104 form a continuous and flexible surface, which increases patient positioning options and patient comfort.

According to an embodiment, upper-angle hinge 110 may comprise a flexible and resilient material such that when upper-angle positioning module 114 is in an unlocked position, upper patient support 106 (and any portion of a patient on the upper patient support 106) may be supported from falling by the force supplied by upper-angle hinge 110. For example, upper-angle hinge 110 may comprise a carbon-fiber reinforced polymer that serves as a flex point and is sufficiently resilient to counter the weight of a patient placed onto the patient positioning device 100.

The forces exerted on the upper-angle hinge 110 by the lower patient support 104, upper patient support 106, and/or the weight of a patient may require a sufficiently rigid hinge, while various positioning configurations may require an upper-angle hinge 110 with great flexibility, all while the upper-angle hinge 110 must be radio-translucent and strong. According to some embodiments, upper-angle hinge 110 comprises one or more layers of fiber, such as, for example, two layers, three layers, or any suitable number of layers of fiber encased in, for example, a polymer, resin, or plastic. According to an embodiment, upper-angle hinge 110 comprises a flexible, spring action that flexes across an area, instead of at a single axis. Additionally, or in the alternative, upper-angle hinge 110 does not flex at a single axis, but curls in the shape of an arc of a circle or an ellipse.

For example, upper-angle hinge 110 may comprise a thin member between the lower patient support 104 and the upper patient support 106 that is substantially thinner than the lower patient support 104 and upper patient support 106. According to some embodiments, a width 130 of upper-angle hinge 110 between lower patient support 104 and upper patient support 106 is approximately 1.50 inches wide, 1.52 inches wide, or 1.59 inches wide. According to some embodiments, width 130 is between approximately 1 inch and 2 inches wide, between approximately 1.25 inches and 1.75 inches wide, or between approximately 1.5 inches and 1.6 inches wide. According to some embodiments, upper-angle hinge 110 is any suitable width 130 sufficient to permit hinged movement between the lower patient support and upper patient support 106.

As just stated, upper-angle hinge 110 may comprise a thin flexible member. According to embodiments, lower patient support 104 and upper patient support 106 comprise a foam board interior that is substantially thicker than the upper-angle hinge 110, which according to some embodiments does not comprise any foam board. Edges of the lower patient support 104 and upper patient support 106 that face the upper-angle hinge 110 may comprise tapered surfaces that support the edges of the upper-angle hinge 110. According to embodiments, upper-angle hinge 110 is between approximately 0.5 and 2.0 mm thick, between approximately 1.4 to 1.7 mm thick, between approximately 1.5 to 1.6 mm thick. According to some embodiments, upper-angle hinge 110 is approximately 1.5 mm or 1.6 mm thick.

Although particular materials are described in connection with the construction of base 102, lower patient support 104, upper patient support 106, and upper-angle hinge 110, embodiments contemplate any suitable polymer or composite, according to particular needs, including but not limited to any fiber-reinforced composite comprising KEVLAR, fiber glass, carbon fiber, hemp, or the like. According to some embodiments, upper-angle hinge 110 comprises joining the upper and lower layers as a composite structure. For example, portions of the lower patient support 104 and upper patient support 106 joined by the upper-angle hinge 110 may be molded as a single piece, such that fibers or filaments in the material extend from a portion on a first side, through a flex point of the upper-angle hinge 110, and into a portion on the second side. Additionally, according to some embodiments, the portion on the first side and the portion on the second side are molded together in a single mold. For example, fibers may extend from a first end of the first portion, through the flex point, and into a second end of the second portion. Additionally, or in the alternative, the angle of a flex point of the upper-angle hinge 110 when molded may be greater than the angle of the flex point when attached to the patient positioning device 100, such that the upper-angle hinge 110 comprises a spring action that naturally elevates the portion of the lower patient support 104 or upper patient support 106 that is not in a locked state.

According to some embodiments, the spring action of the upper-angle hinge 110 is controlled by the thickness and geometry of the hinge. Where the upper-angle hinge 110 couples the lower patient support 104 and upper patient support 106, the force supplied by the upper-angle hinge may be sufficient to support a portion of a patient's weight placed on the upper patient support 106. In this way, a technician using the patient-positioning device may adjust the upper-angle 602 (See FIGS. 6A-6D) without supporting the weight of the patient while the upper-angle positioning module 114 is in an unlocked state. For example, when a patient is placed on the lower patient support and upper patient support 106, upper-angle hinge 110 may permit adjustment of one or more angles of the patient to permit focused and unobstructed treatment or imaging of, for example, the breast or lungs of a patient. Positioning of a patient with respect to the upper-angle 602 will be discussed in more detail below.

Figure 2:
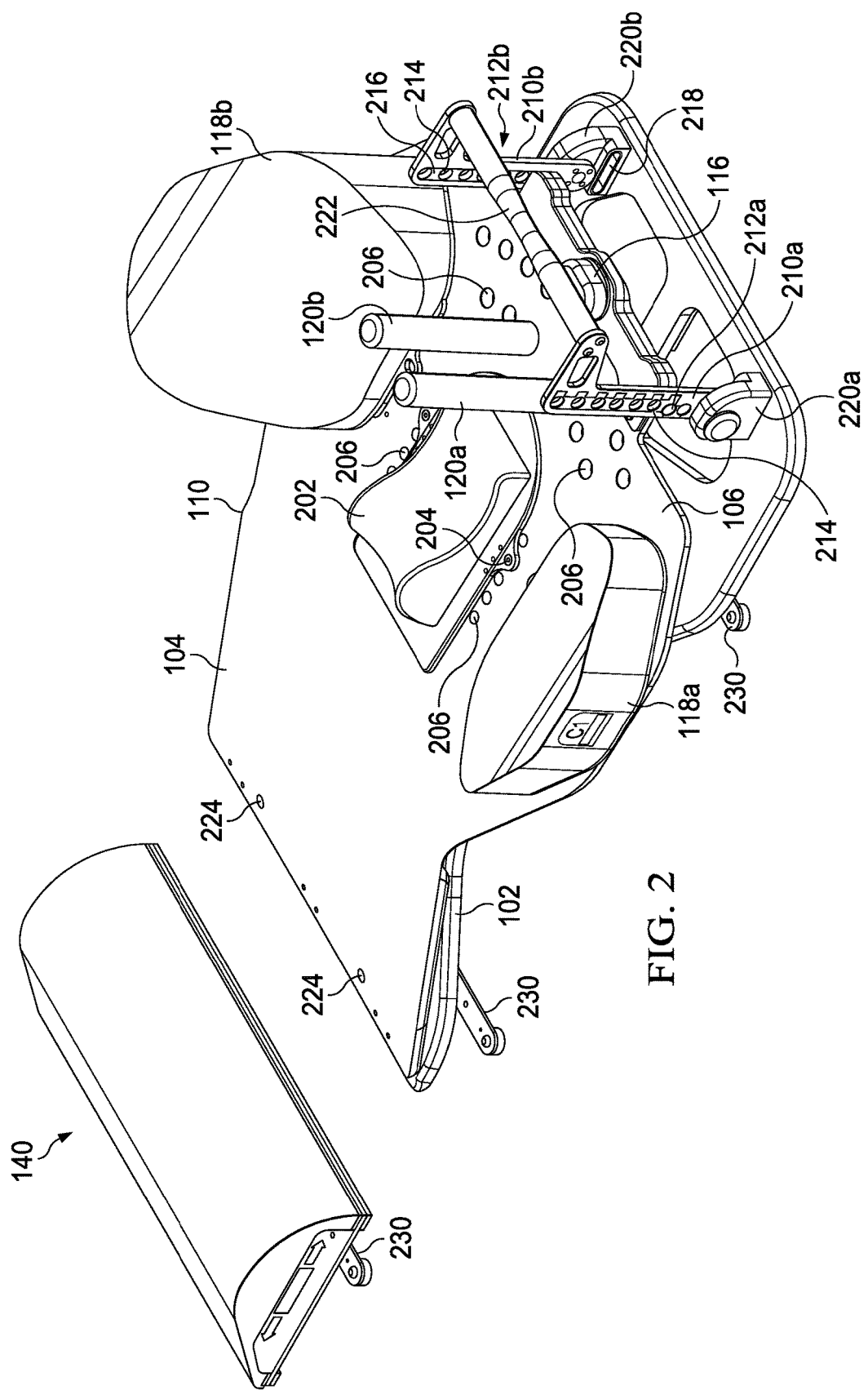
FIG. 2 illustrates a perspective view of an exemplary patient positioning device according to an embodiment.

FIG. 2 illustrates a perspective view of patient positioning device 100 according to an embodiment. Arm positioning bolsters 118a-118b, hand grips 120a-120b, and neck positioning module 202 may couple to upper patient support 106. According to embodiments, upper patient support 106 comprises one or more positioning holes 206 that provide coupling and adjustment between various configurations of neck-positioning module 202, arm-positioning bolsters 116a-116b, and arm-positioning hand grips 120a-120b. For example, dowels 204 on underside of neck positioning module 202 may be received by positioning holes 206 to provide for a secure, removable, adjustable, and repeatable placement of neck positioning module 202, as described more fully below. Arm-positioning bolsters 116a-116b, arm-positioning hand grips 120a-120b, and additional modules may be coupled to upper patient support 106 and lower patient support 104 in a similar manner, according to particular needs.

Upper patient support 106 may adjustably couple to armatures 210a-210b. For example, upper patient support 106 may comprise upper-angle positioning module 114 which comprises upper-angle lock knob 116. Upper-angle lock knob 116 is communicatively coupled to one or more pins 212a-212b, which are received in one or more apertures 214, one or more vertical slots 216, and/or one or more horizontal slots 218 in armatures 210a-210b. Turning upper-angle lock knob 116 may control the extension and retraction of the one or more pins 212a-212b and thereby the coupling to armatures 210a-210b to provide for the adjustment of the upper-angle 602 of upper patient support 106 in relation to lower patient support 104 and base 102. Armatures 210a-210b may couple to base 102 by one or more armature hinges 220a-220b and to each other by handle 222.

Neck-positioning module 202 may comprise an angled surface that is contoured to the shape of the back of a patient's neck and head. According to some embodiments, neck-positioning module 202 is movable with respect to upper patient support 106 to allow proper placement of the patient's head and neck with respect to a radiation source. According to some embodiments, neck-positioning module 202 comprises dowels 204 on either side of the module that are received by positioning holes 206 in the surface of the upper patient support 106. Dowels 204 may be inserted into various positioning holes 206 to allow different positions of the neck-positioning module with respect to the upper patient support 106.

Neck-positioning module 202 may removably couple to the upper patient support 106 in a variety of positions. Each of the dowels 204 and/or positioning holes 206 may be indexable so that the neck positioning-module 202 may be coupled to the upper patient support 106 reproducibly in the same location. According to embodiments, neck positioning module 202 may comprise two dowels 204 (one on each of a left side and a right side) which may couple to any two positioning holes 206 (one each on a left side and a right side) of the ten positioning holes 206 on upper patient support 106, which permits neck-positioning module 202 to adjust between five positions. Although neck-positioning module 202 is illustrated as comprising two dowels 204 and upper patient support 106 is illustrated as comprising ten positioning holes 206, embodiments contemplate any number of dowels 204 or positioning holes 206, according to particular needs.

Neck positioning module 202 may be shaped to receive the neck and head of a patient and adequately support such positioning for the duration of a radiation treatment in a comfortable and stable manner. According to embodiments, various configurations and types of neck-positioning modules 202 may be provided with patient positioning device 100 such that patient positioning device 100 may accept patients in a supine position, patients of different heights or shapes, and patients in different positions. According to some embodiments, neck positioning modules 202 may attach to various types of headrests, such as a gel donut, headrest adaptor, or head and neck immobilization modules (such as head immobilization module 1000 (FIG. 10)) according to particular needs.

Ann-positioning bolsters 118a-118b may comprise an angled upper surface that slants upward and away from a centerline of the surface of upper patient support 106 and provide support for the arms of a patient. According to some embodiments, arm-positioning bolsters 118a-118b are provided as a set of multiple interchangeable sizes to adequately position patients with different sized arms and bodies and/or to position arms in different positions with respect to the radiation source or imaging device. According to embodiments, arm-positioning bolsters 118a-118b comprise foam pads of different thickness that provide different angles and heights to support arms of a patient while laying on patient positioning device 100. For example, a thick foam pad may cause the arms of a patient to be pushed toward the patient and in an upward manner. A thin foam pad may cause the arm of a patient to open outward, and, for example, more easily expose a breast or other treatment area of a patient for better treatment or imaging. Although patient positioning device 100 is illustrated as comprising two arm-positioning bolsters 118a-118b, embodiments contemplate any number, including zero, arm-positioning bolsters 118a-118b, according to particular needs. For example, when patient positioning device 100 is used in conjunction with a vacuum cushion or other accessory, a therapist may wish not to use arm-positioning bolsters 118a-118b to provide a better fit for a patient.

According to some embodiments, arm-positioning bolsters 118a-118b are movable with respect to upper patient support 106 and are attached by one or more dowels 204 that couple to positioning holes 206 in the surface of upper patient support 106. Each of the arm-positioning bolsters 118a-118b may be movable in an inferior or superior position or in any other suitable positions, according to particular needs.

Hand grips 120a-120b may provide a gripping support structure to a patient to support the hands during radiation treatment. When treating a patient in the chest or thorax area, the patient's arms usually need to be out of the way. Hand grips 120a-120b provide for allowing the patient to keep their arms in a stable position out of the way of an image or treatment beam. According to some embodiments, a patient may support his or her hands on handle 222.

Hand grips 120a-120b may be contoured to provide a comfortable gripping surface. According to some embodiments, hand grips 120a-120b are movable with respect to upper patient support 106 and are attached by insertion of one or more dowels 204 into one or more positioning holes 206 in the surface of upper patient support 106. According to embodiments hand grips 120a-120b each comprise one dowel 204 that each couple to one of fourteen different positioning holes 206 in the surface of upper patient support 106. Although hand grips 120a-120b are each illustrated with a single dowel and upper patient support 106 is illustrated with fourteen positioning holes 206, embodiments contemplate any suitable number of dowels 204 or positioning holes 206 according to particular needs.

Because each of neck positioning module 202, arm-positioning bolsters 118a-118b, and hand grips 120a-120b may be located in one or more positions, patient positioning device 100 comprises an indexing system for positioning holes 206 that provide a label so that each of neck positioning module 202, arm-positioning bolsters 118a-118b, and hand grips 120a-120b may be removed and replaced in the same position for each patient. Because patient positioning device 100 may be used for the same patient over multiple treatment or imaging sessions and for different patients, indexing system provides for a system to reproducibly position the patient positioning device 100 and components of the patient positioning device 100 so that positioning may only have to be determined a first time.

According to some embodiments, patient positioning device 100 comprises a plurality of vacuum cushion receptacles 224 that receive one or more protrusions on a vacuum cushion indexing module 810 (See FIG. 8). According to embodiments, vacuum cushion indexing module 810 comprises a plastic member that couples to lower patient support 104 of patient positioning device to index and lock in a vacuum cushion. A vacuum cushion provides for increased patient support for various treatment and imaging procedures by molding itself to a particular patient's body. According to embodiments vacuum cushion indexing module 810 provides for reproducibly coupling the vacuum cushion to the patient positioning device 100 in substantially the same configuration.

For example, embodiments of the patient positioning device 100 are particularly effective at positioning a patient for radiological treatment or imaging of a patient's breast, chest, or thorax, including breast and lung cancer. According to particular embodiments, patient positioning device 100 provides for reproducibly producing a setup of a patient during an initial imaging or treatment session during subsequent treatment sessions, even when the sessions are days, weeks, or months apart. For example, during an initial session, a therapist may image a patient to determine the exact location, size, and type of tumor present in a patient. The therapist may then need an amount of time to develop a plan for treatment. The next patient session may be days, weeks, or months later, and embodiments of the patient positioning device 100 provide for reproducing the initial setup in an almost exact setup during subsequent sessions.

To facilitate reproducing the initial setup, embodiments contemplate providing an indexing system that reproducibly locates every positionable component of the patient positioning device 100, such as, for example, initial angle 600, upper angle 602, neck-positioning module 202, arm-positioning bolsters 118a-118b, hand grips 120a-120b, base 102, and patient support 140. According to some embodiments, indexing system may comprise a ruler that is coupled to one or more sides of patient positioning device 100 that allows the patient positioning device to be aligned with a laser for exact positioning of a treatment beam with respect to a patient and to patient positioning device 100.

Figure 3:
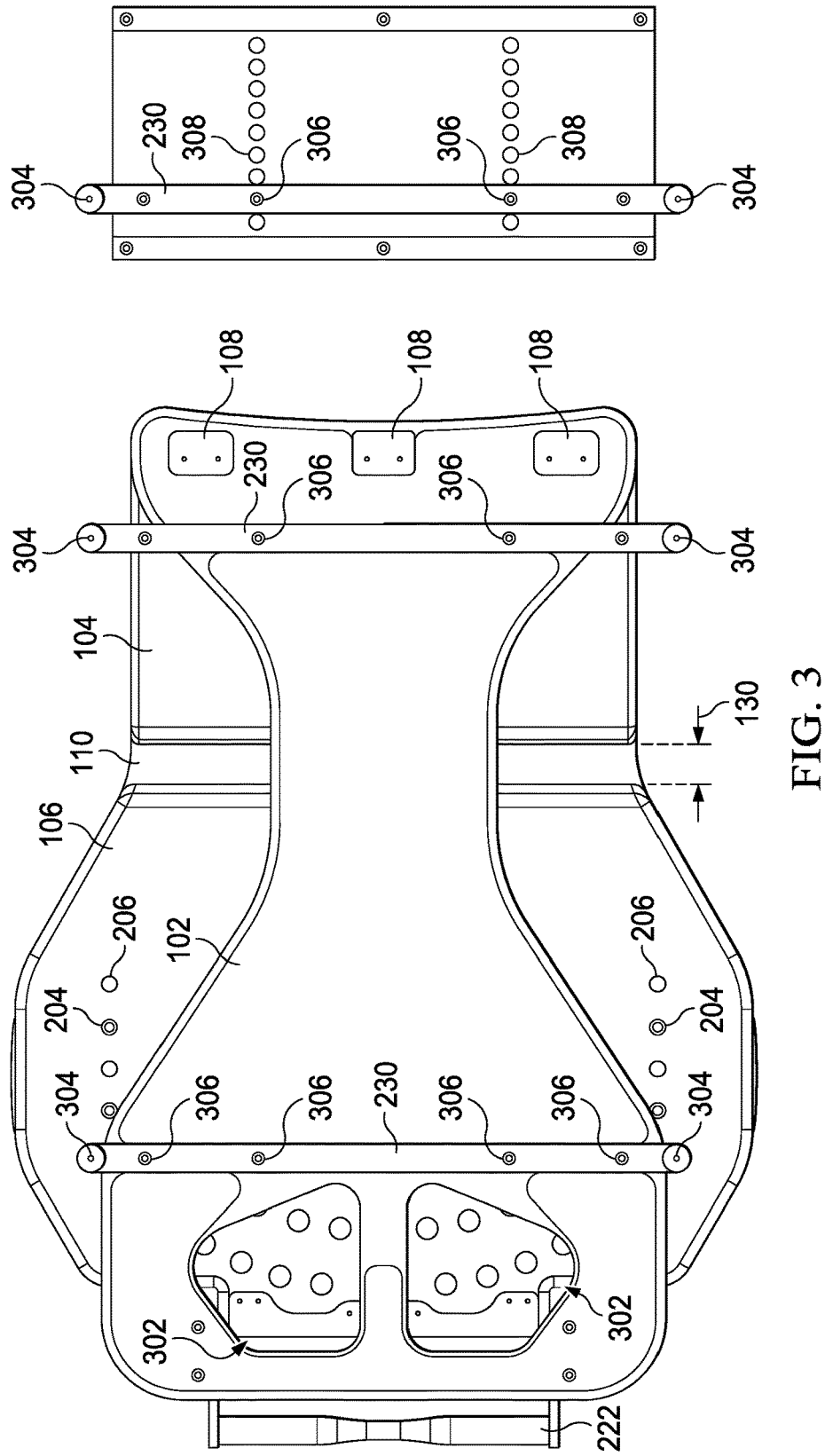
FIG. 3 illustrates a bottom view of an exemplary patient positioning device according to an embodiment.

FIG. 3 illustrates a bottom view of patient positioning device 100 according to an embodiment. According to some embodiments, base 102 of patient positioning device 100 comprises a substantially flat and couch-indexable substrate to which one or more components of the patient positioning device 100 may attach. In some embodiments, base 102 comprises a radio-translucent material and is shaped to minimize interaction with a radiation beam path, such as, for example, an hourglass-type shape. According to some embodiments, an hourglass-type shape comprises a first end of a width approximately equal to a width of a second end and comprising a restricted portion in the middle that is of minimal width but still maintains rigidity of the base. According to other embodiments, base 102 comprises any suitable shape that minimizes interaction with a beam path. For example, when treating a patient, a radiation beam may arrive at an angle to the patient. The restricted portion of the base 102 may permit a radiation beam to avoid base 102 increasing the efficacy of the beam. According to some embodiments, base 102 comprises openings 302 that may further decrease weight of base 102 and minimize interaction with a radiation beam.

Base 102 may couple to a treatment couch by one or more removable and interchangeable index bars 230 comprising pins 306 that couple to one or more receptacles 308 in the under surface of base 102. Similarly, patient stop 140 may couple to a treatment couch 800 (FIG. 8) by index bars 230, whereby pins 306 couple to one or more receptacles 308 in the under surface of patient stop 140. Base 102 and patient stop 140 may couple by index bars 230 to a treatment couch 800 wherein index bar tabs 304 couple to similarly shaped slots 802 in the surface of the treatment couch 800 so that patient positioning device 100 and patient stop 140 are securely and removably coupled to the treatment couch 800 and may be repeatably placed in the same position after the patient positioning device 100 and patient stop 140 are removed, as described in more detail below.

Figure 4:
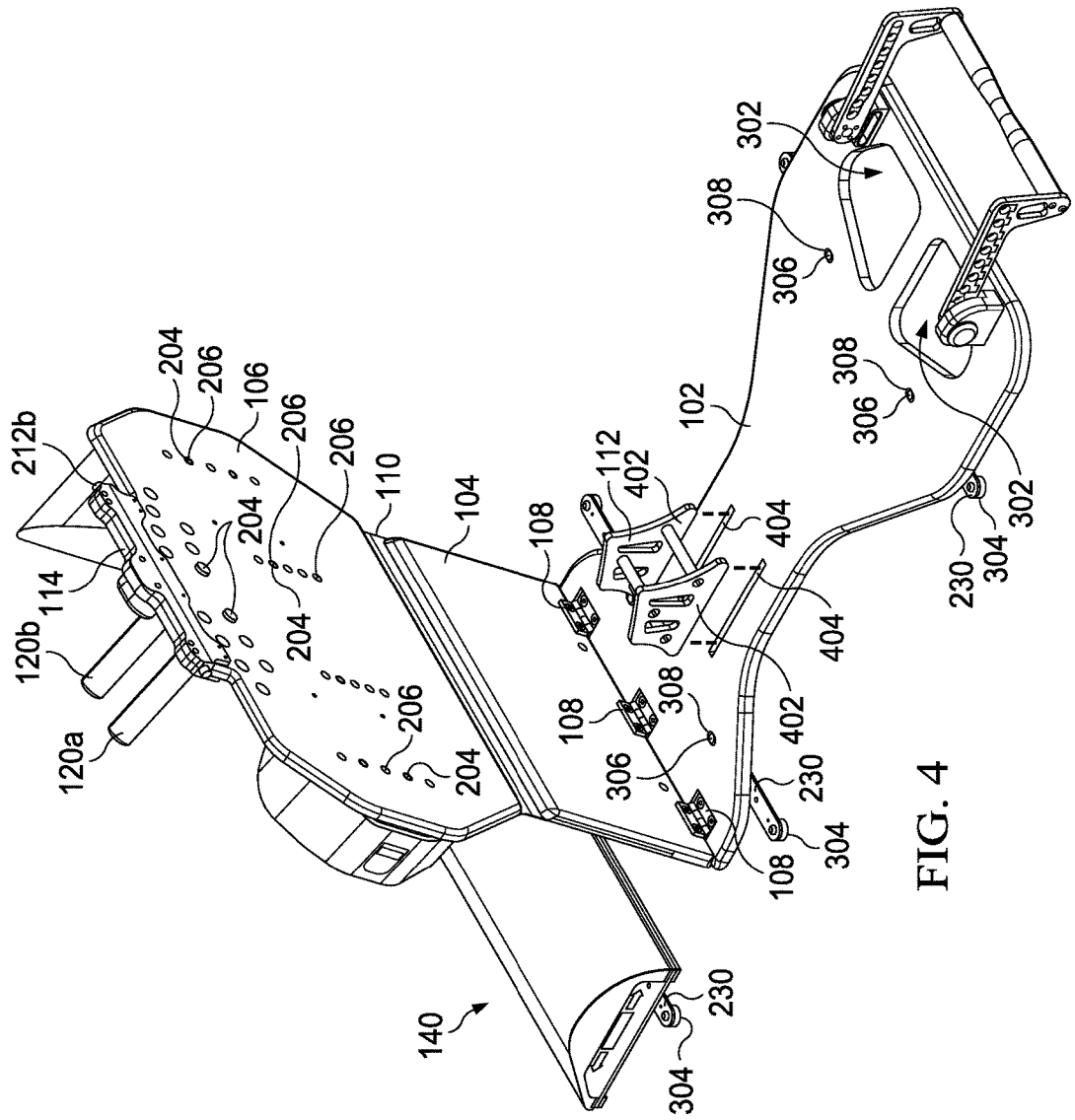
FIG. 4 illustrates a perspective view of an exemplary patient positioning device in an open configuration according to an embodiment.

FIG. 4 illustrates a perspective view of an exemplary patient positioning device 110 in an open configuration according to an embodiment.

According to some embodiments, base 102 of patient positioning device 100 comprises a substrate to which one or more components may couple, such as the initial-angle support 112, armatures 210a-210b, and lower-angle support 102. According to some embodiments, base 102 comprises a carbon-fiber reinforced polymer, or any other suitable polymer, including but not limited to any suitable fiber-reinforced polymer, comprising, for example, KEVLAR, fiber glass, hemp, or the like, including the foregoing sandwiched over a low density core of foam or other suitable material. According to some embodiments, initial-angle positioning module 112 may couple base 102 to lower patient support 104. According to some embodiments, more than one initial-angle positioning modules 112 may be used to couple lower patient support 104 to base 102.

For example, patient positioning device 110 may comprise an initial-angle support module 112 comprising one or more feet 402 that couple to corresponding slots 404 in base 102. Although illustrated as two feet 402 coupling to two slots 404, embodiments contemplate any suitable number of feet 402 and slots 404, according to particular needs, or any suitable method for coupling initial-angle support module 112 to base 102 and/or lower patient support 104.

Initial-angle support module 112 provides for locking the initial angle 600 (FIG. 6) of the patient positioning device 100, such as for example, the angle of the hinge 108 between base 102 and lower patient support 104. A therapist positioning a patient on patient positioning device 100 may choose an initial-angle support module 112 corresponding to an initial angle 600 that the therapist determines is suitable for the proper treatment or patient, and places the feet 402 of initial-angle support module 112 in slots 404 of base 102. When the patient is lowered, the lower surface of the lower patient support 104 rests against an upper portion of the initial-angle support module 112 to firmly hold lower patient support 104 at the desired angle with respect to the base 102. Initial-angle support module 112 may be provided with patient positioning device in one or more preset angles, such that the initial angle 600 is chosen by placing an initial-angle support module 112 that corresponds with the angle desired. Initial-angle support modules 112 may be provided with angles of, for example, 5 degrees, 10 degrees, 15 degrees, 20 degrees, 25 degrees, 30 degrees, or any other suitable angle. Because the initial-angle support modules 112 comprise preset angles, changing the initial angle 600 is easy and quick. The patient simply sits up or is lifted up and a different initial-angle support module 112 is inserted to set the new desired angle.

According to some embodiments, the initial-angle support module 112 comprises an adjustable wedge. In these embodiments, the wedge couples with base 102 by a series of interlocking channels on the wedge or base 102. The wedge may be slideably coupled with these channels such that the wedge is movable with respect to base 102, and the lower patient support 104 rests on a top portion of the wedge, which adjusts initial angle 600 of the lower patient support 104 with respect to base 102. According to some embodiments, initial angle 600 is increased by sliding the wedge with respect to the base 102 in a first direction, and initial angle 600 is decreased by sliding the wedge with respect to the base 102 in a second direction. According to some embodiments, initial-angle support module 112 wedge comprises a non-metallic, plastic, or low-density non-metallic material. According to some embodiments, the wedge may be secured in a rotated or flipped position such that different angles of initial angle 600 may be selected with the same wedge. According to some embodiments, initial angle 600 is selected with pins and lateral supports comprising apertures coupled to lower patient support 104 and the base 102 as described in more detail in connection with the upper-angle positioning module 114 below. According to some embodiments, initial angle 600 may also be set by swapping the wedge to another size.

According to some embodiments, initial angle 600 is determined by a therapist based on the location or type of tumor present in a patient. For example, prior to a patient being positioned on patient positioning device 100, the patient may have already been diagnosed with cancer, and the general location of the cancer may be known. Accordingly, a therapist may know that when a tumor is present in a breast, a particular size for an initial-angle positioning module 112 is needed. For a tumor present in the upper lungs, a different size may be needed, such as a substantially flat initial angle 600. Based on the location of the tumor, the therapist may create one or more protocols that determine a first initial angle 600 to try for a patient. According to conventional patient positioning devices 100, a therapist may not have been able to determine a first initial angle 600 prior to patient positioning because conventional patient positioning devices 100 lack a positionable upper angle 602 (See FIG. 6). Because of the secondary positionable upper angle 602, patient positioning device 100 provides for therapists being able to adjust for individual patient anatomy without readjusting the initial angle 600. For example, when a patient lies down, the patient's particular anatomy may cause the patient's chin to tuck into their chest. Embodiments of the patient positioning device 100 of the current disclosure provide for adjusting the upper patient support 106 independently of the lower patient support 104 to move the patient's chin away from the chest. Similarly, the clavicle of a particular patient may be in a substantially closed position based on an initial angle 600 of the lower patient support 104. By adjustment of the upper angle 602, patient positioning device 100 provides for moving the patient's arms in a clavicle-open position without having to lift the patient off of the patient positioning device 100. This may be especially useful for patients with limited mobility or painful joints, or patients who may not otherwise be able to tolerate a particular position long enough for treatment.

Once the initial angle 600 is set and the patient support is lowered until the lower patient support 104 rests on initial-angle support module 112 which is properly placed in base 102, the upper-angle positioning module 114 may be coupled to armatures 210a-210b to set the upper angle 602.

As discussed above, upper patient support 106 may comprise upper-angle positioning module 114 that couples upper patient support 106 to one or more armatures 210a-210b.

Figure 5A:
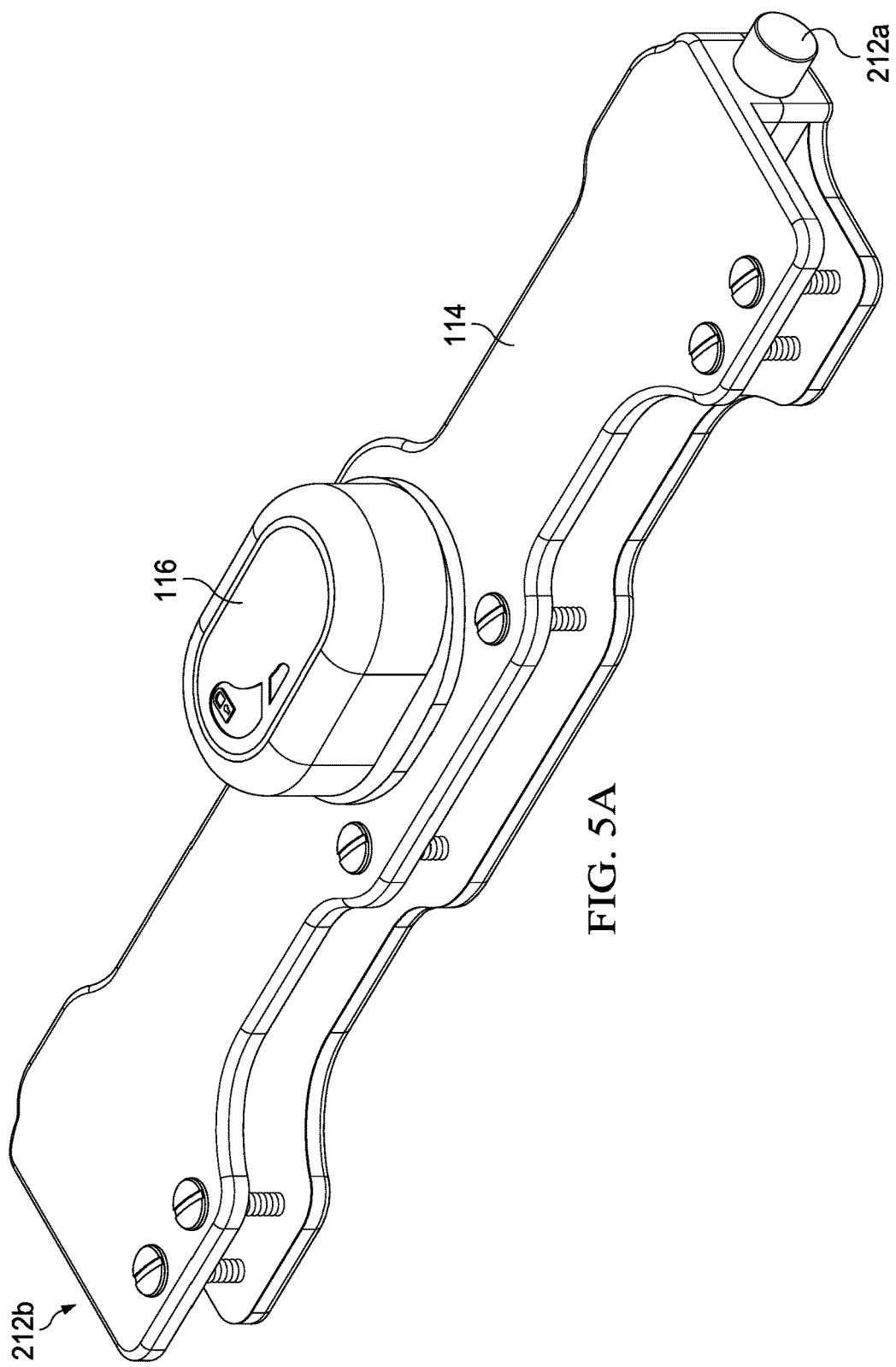
FIGS. 5A-5B illustrate an exemplary upper-angle positioning module according to embodiments.
Figure 5B:
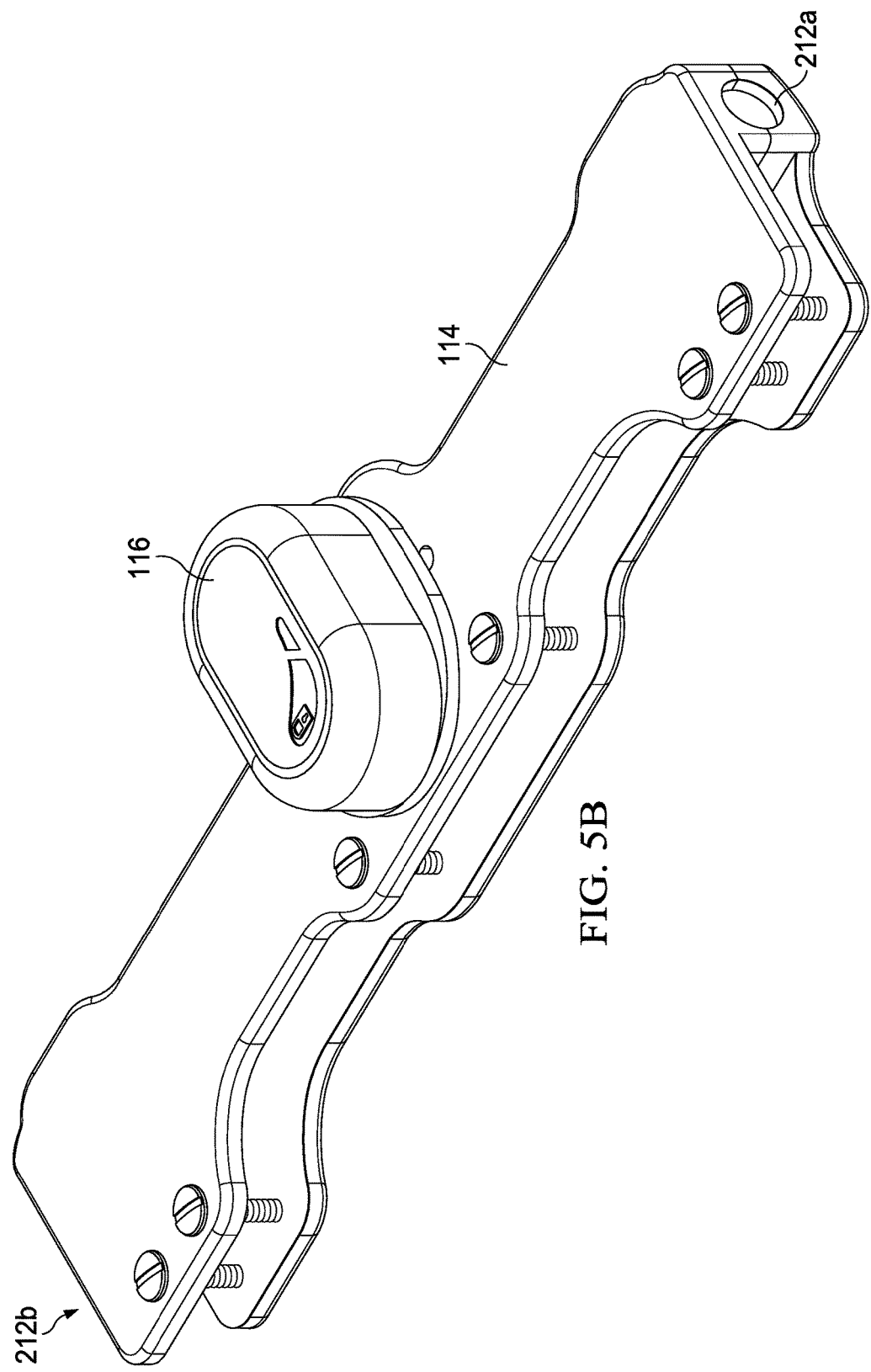

FIGS. 5A-5B illustrate an exemplary upper-angle positioning module 114 according to embodiments.

FIG. 5A illustrates an exemplary upper-angle positioning module 114 with upper-angle lock knob 116 in a locked position. When upper-angle lock knob 116 is in a locked position, pins 212a-212b may be in an extended position.

FIG. 5B illustrates an exemplary upper-angle positioning module 114 with upper-angle lock knob 116 in an unlocked position. When upper-angle lock knob 116 is in an unlocked position, pins 212a-212b may be in a retracted position.

Although upper-angle lock knob 116 and pins 212a-212b are illustrated in a particular configuration and with two settings, embodiments contemplate upper-angle lock knob 116 comprising any number of settings. For example, armatures 210a-210b comprise apertures 214 and vertical slot 216. Embodiments contemplate that when upper-angle lock knob 116 is turned to a first position, pins 212a-212b may engage with apertures 214 so that the pins 212a-212b are substantially inserted into apertures 214 and lock upper patient support 106 in a fixed position with respect to armatures 210-210b. When upper-angle lock knob 116 is turned to a second position, pins 212a-212b may retract from apertures 214, but remain slidably coupled with vertical slot 216. In this way, upper patient support 106 may be moved up and down in relation to base 102 while remaining engaged to armatures 210a-210b. Additionally, embodiments contemplate that upper-angle lock knob 116 may be turned to a third position such that pins 212a-212b retract more fully and are no longer engaged to apertures 214 or vertical slot 216. In this manner, upper patient support 106 may no longer be coupled to armatures 210a-210b.

In this manner, upper angle 602 is adjustable through various angles by insertion of pins 212a-212b in higher or lower apertures 214 on armatures 210a-210b. According to some embodiments, armatures 210a-210b are coupled with base 102 by rotating hinges 220a-220b that provide for armatures 210a-210b to be moved through various angles with respect to upper patient support 106 and base 102. One or more additional attachment mechanisms may couple any suitable upper-angle positioning module to base 102.

According to some embodiments, handle 222 couples to armatures 210a-210b and comprises a locking mechanism and/or a synchronization mechanism. According to some embodiments, handle 222 couples pins 212a-212b to the same lateral plane so that the pins 212a-212b are substantially aligned with corresponding apertures 214 in each of armatures 210a-210b. Additionally, handle 222 may comprise a sufficiently rigid and strong material such that it can support the weight of patient-positioning device 100 when carried by handle 222. According to some embodiments, handle 222 may be used to place patient positioning device 100 in a substantially flat position. For example, in some embodiments, initial-angle positioning module 112 may be removed and handle 222 may be used to slide armatures 210a-210b away from a perpendicular position with respect to base 102, so that the lower and upper patient supports 104-106 lay substantially flat against base 102. According to some embodiments, upper-angle positioning module 114 may be locked at the lowest aperture 214 or horizontal slot 218 in armatures 210a-210b to secure lower patient support 104 and upper patient support 106 in a substantially flat position.

According to some embodiments, upper-angle hinge 110 comprises a spring-like action that exerts force to support all or a portion of the weight of upper patient support 106, any attached modules, and/or the portion of a patient's weight that is resting on upper patient support 106. This provides for keeping upper patient support 106 in an elevated position even when pins 212a-212b are not fully engaged with armatures 210a-210b. According to some embodiments, this provides for easier repositioning of a patient because the patient may stay reclined on the upper patient support 106 while the therapist raises and/or lower the upper patient support 106. According to some embodiments, this provides for one-handed repositioning of the upper patient support 106.

FIGS. 6A-6D illustrate an exemplary patient positioning device 100 with an assortment of exemplary initial-angle positioning modules 112 according to embodiments.

Figure 6D:
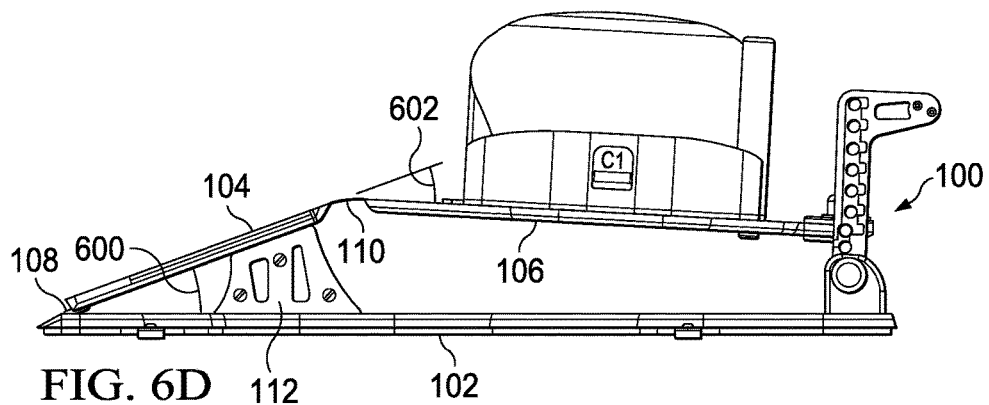
FIGS. 6A-6D illustrate an exemplary patient positioning device with an assortment of exemplary initial-angle positioning modules according to embodiments.
Figure 6C:
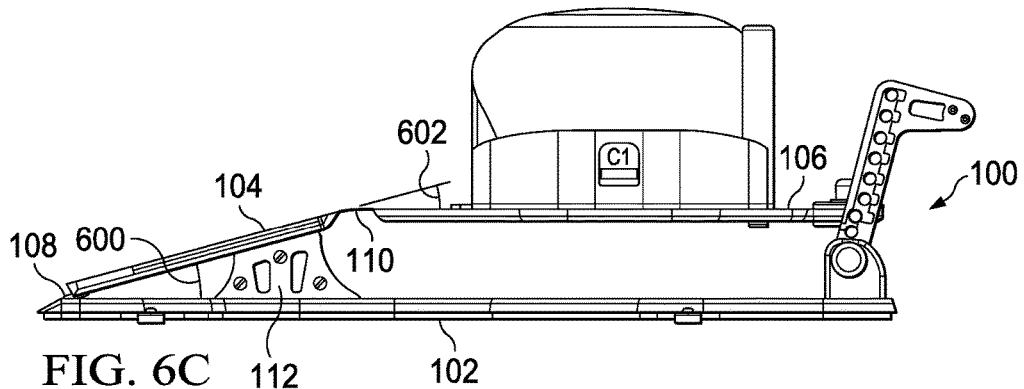
Figure 6B:
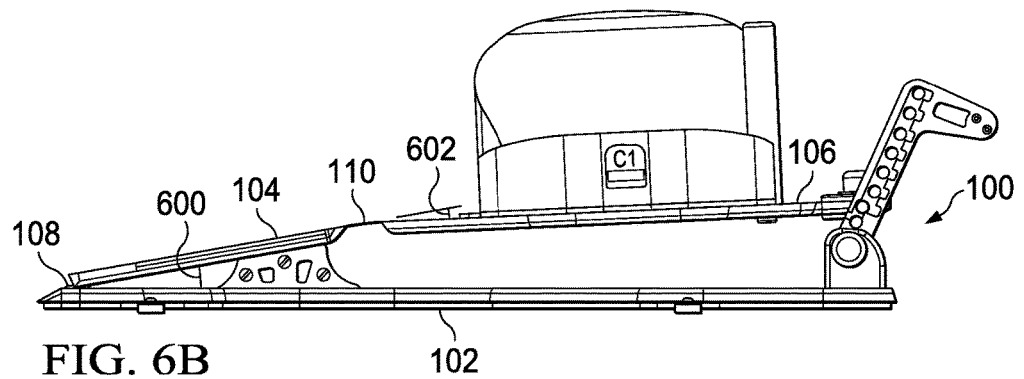
Figure 6A:
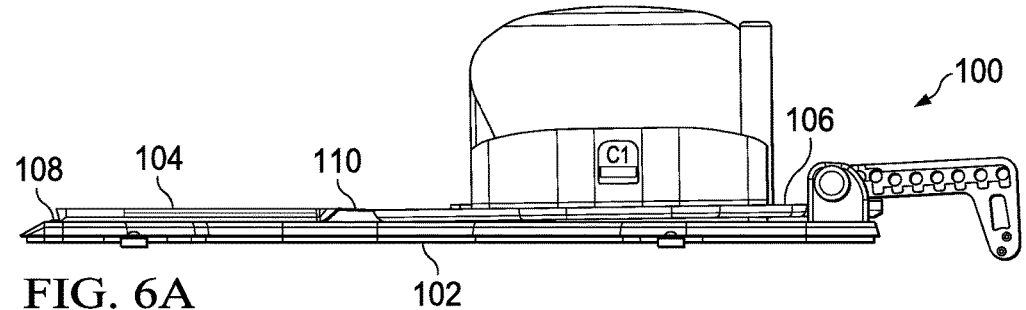

FIG. 6A illustrates a patient positioning device 100 with no initial-angle support module 112. According to this embodiment, patient positioning device 100 may comprise a configuration suitable for storage or for a horizontal position of patient. According to this embodiment, lower surfaces of lower patient support 104 and upper patient support 106 rest directly on an upper surface of base 102 and angle of hinge 108 is approximately zero degrees. In this configuration, upper-angle hinge 110 may remain substantially flat and comprise an angle of approximately 180 degrees. Upper-angle positioning module 114 may couple armatures 210a-210b by horizontal slot 218, such that the patient positioning device 100 may remain in a substantially flat configuration for treatment or storage.

FIG. 6B illustrates a patient positioning device 100 with an initial-angle support module 112 comprising 10 degrees. According to this embodiment, an initial angle 600 may be set to 10 degrees by inserting the 10 degree initial-angle support module 112 into base 102. Upper-angle 602 may be adjusted by unlocking upper-angle lock knob 116 and repositioning pins 212a-212b into different apertures 214 of armatures 210a-210b.

FIG. 6C illustrates a patient positioning device 100 with an initial-angle support module 112 comprising 15 degrees. According to this embodiment, an initial angle 600 may be set to 15 degrees by inserting the 15 degree initial-angle support module 112 into base 102. Upper angle 602 may then be adjusted by repositioning pins 212a-212b into different apertures 214 of armatures 210a-210b.

FIG. 6D illustrates a patient positioning device 100 with an initial-angle support module 112 comprising 20 degrees. According to this embodiment, an initial angle 600 may be set to 20 degrees by inserting the 20 degree initial-angle support module 112 into base 102. Upper angle 602 may then be adjusted by repositioning pins 212a-212b into different apertures 214 of armatures 210a-210b.

Although FIGS. 6A-6D illustrate particular initial-angle support modules 112, embodiments contemplate any number or combination of initial-angle support modules at any suitable angle according to particular needs. Additionally, although initial angle 600 may be set by initial-angle support modules 112, embodiments contemplate any suitable manner of selecting initial angle 600 including, for example, wedges, armatures, locking mechanism, hinges, or the like.

Figure 7C:
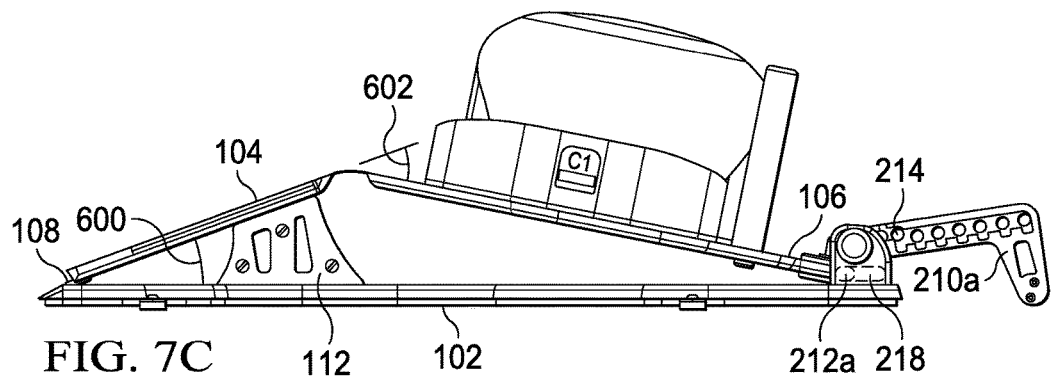
FIGS. 7A-7C illustrate an exemplary patient positioning device with an assortment of exemplary upper angle positions according to embodiments.
Figure 7B:
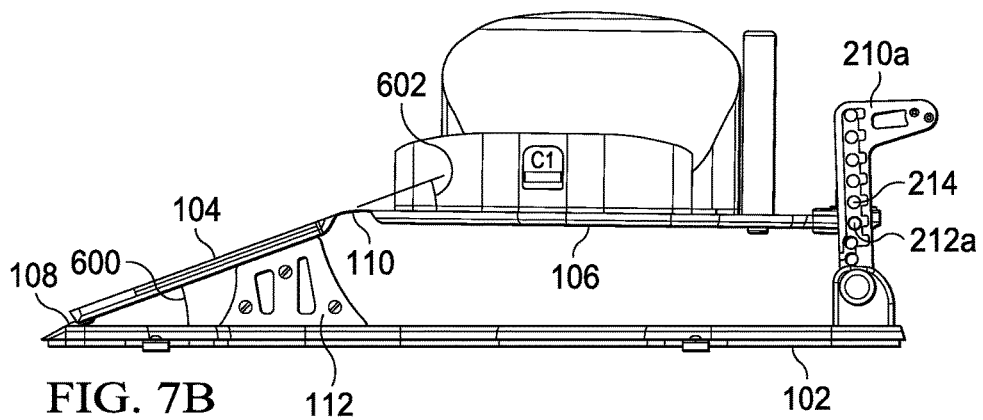
Figure 7A:
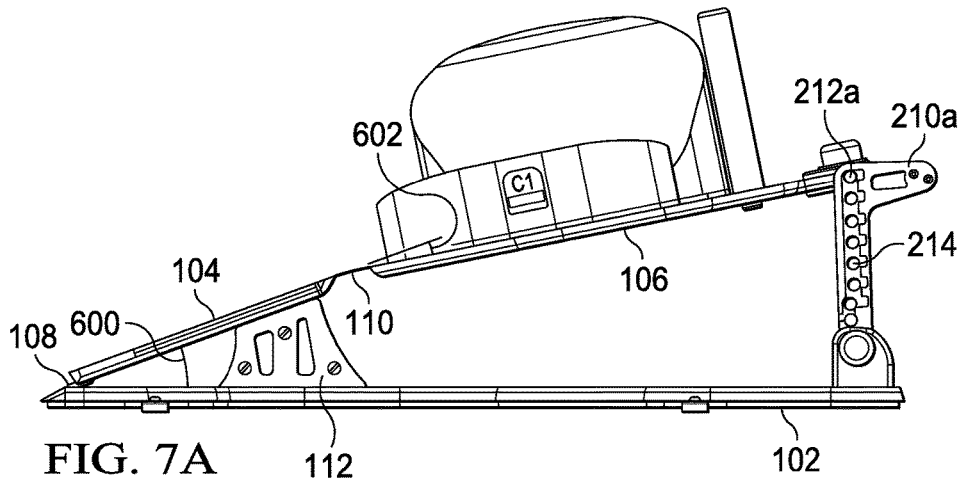

FIGS. 7A-7C illustrate an exemplary patient positioning device 100 with various upper angle 602 configurations. Once an initial angle 600 is set by initial-angle support module 112, upper angle 602 may be set by repositioning pins 212a-212b into one or more of apertures 214, vertical slot 216, or horizontal slot 218. As discussed above, armatures 210a-210b may comprise one or more apertures 214 that are configured to receive pins 212a-212b to provide for positioning of upper patient support 106. Although armatures 210a-210b are illustrated with eight apertures 214 in a substantially vertical configuration, embodiments contemplate any number or configuration of apertures 214 according to particular needs.

FIG. 7A illustrates a patient positioning device 100 with an initial-angle support module 112 comprising 20 degrees and upper-angle support module 114 locked in an eighth aperture 214. This provides for an initial angle 600 of 20 degrees and a shallow upper angle 602.

FIG. 7B illustrates a patient positioning device 100 with an initial-angle support module 112 comprising 20 degrees and upper-angle positioning module 114 locked in a third aperture 214. This provides for an initial angle 600 of 20 degrees and an increased upper angle 602.

FIG. 7C illustrates a patient positioning device 100 with an initial-angle support module 112 comprising 20 degrees and upper-angle positioning module locked in horizontal slot 218. This provides for an initial angle 600 of 20 degrees and a large upper angle 602.

By adjusting the initial angle 600 and upper angle 602, a patient may be positioned in various positions that provide for increased patient comfort and more direct targeting of a target area of patient for treatment or imaging.

FIG. 8 illustrates an exemplary patient positioning device 100 coupled to an exemplary treatment couch 800 according to an embodiment. As illustrated treatment couch 800 couples to patient positioning device 100 by tabs 304 of index bars 230 by coupling with slots 802 of treatment couch 800. Although illustrated with particular index bars 230, various treatment couches 800 comprise proprietary index bars 230. Embodiments of patient positioning device 100 comprise any suitable coupling mechanism to reproducibly position patient positioning device 100 in substantially the same placement on a treatment couch 800.

In a similar manner, patient stop 140 may couple with one or more index bars 230 that reproducibly couple patient stop 140 to the same spot of a treatment couch 800. For example, as illustrated patient stop 140 may comprise nine indexable positions that allow the patient stop 140 to be positioned in nine positions relative to an index bar 230. This provides for various ranges of patient positions due to the various body types of patients that may need to be treated or imaged. Although patient stop 140 is illustrated with nine indexable positions, embodiments contemplate any suitable number of indexable positions according to particular needs.

While patient positioning device 100 is securely coupled to treatment couch 800 it may be raised and inserted though radiological imager 804. Although patient positioning device 100 is depicted as coupling to treatment couch 800 with tabs 304 and slots 802, embodiments contemplate any suitable coupling between patient positioning device 100 and treatment couch 800 according to particular needs.

According to some embodiments, patient positioning device 100 comprises a patient alignment scale 812. Patient alignment scale 812 may comprise a millimetric rule coupled to a side of patient positioning device 100 that permits alignment for treatment or imaging. For example, a treatment and/or patient setup room may comprise a laser guide that projects a laser on a fixed position in the room in relation to the beam guide. A therapist may align the patient positioning device 100 in relation to the laser to ensure the target area of the patient is exactly aligned with the treatment beam.

Figure 9:
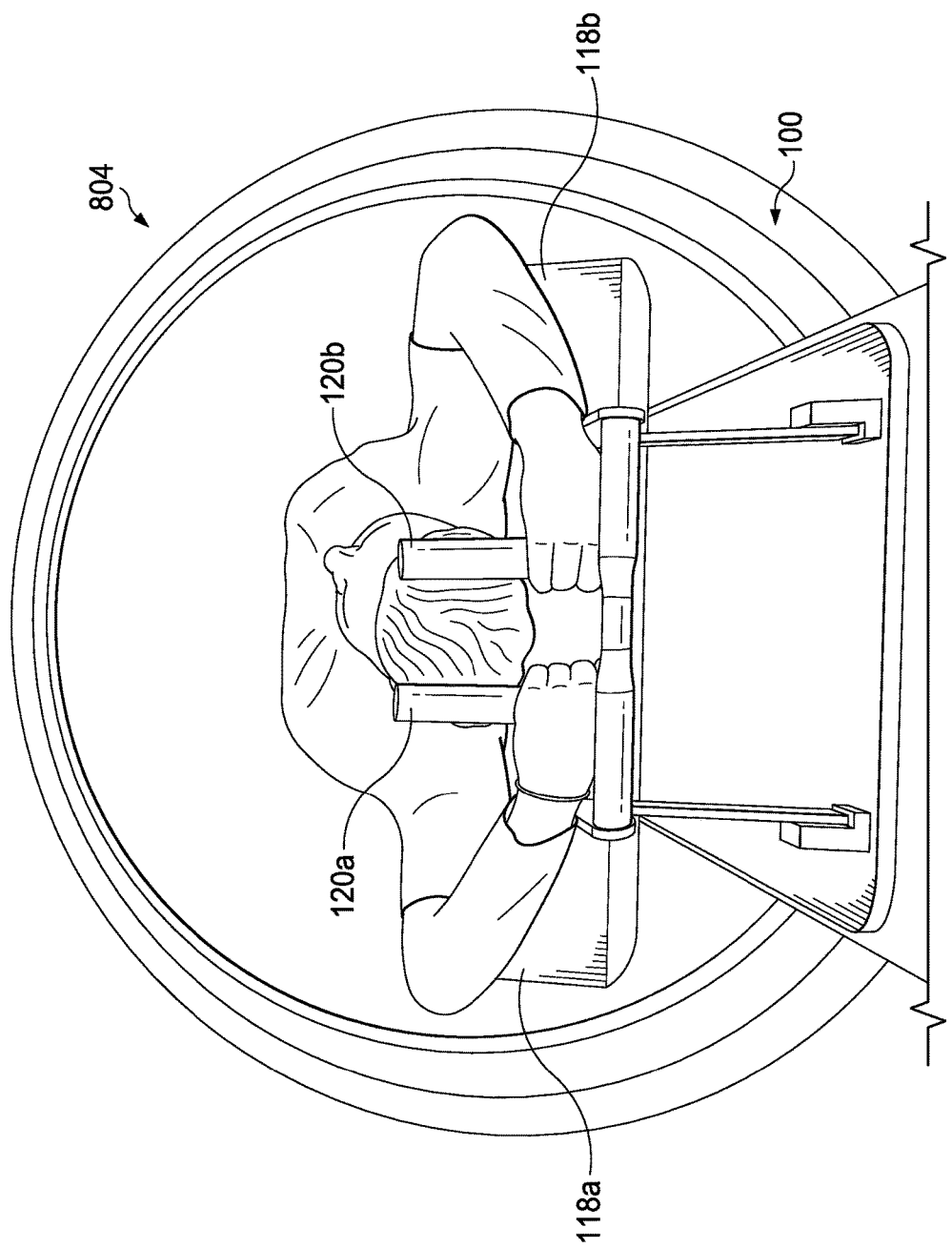
FIG. 9 illustrates a patient receiving radiological imaging by patient positioning device.

FIG. 9 illustrates a patient receiving radiological imaging on patient positioning device 100. According to embodiments, a patient may be placed inside of radiological imager 804 to image any cancer, tumor, or other area of investigation inside a patient's body.

A patient may be positioned on patient positioning device 100 with the patient's arms resting on arm bolsters 118a-118b and hands gripping hand grips 120a-120b. Patient may be placed inside radiological imager 804 to image any internal condition. After imaging is completed, a technician may note the precise positioning of the patient and record each of the indexed points of patient positioning device 100 and any attached modules. In this manner, patient may be repositioned in substantially the same position for treatment of any disease detected during imaging.

Figure 10:
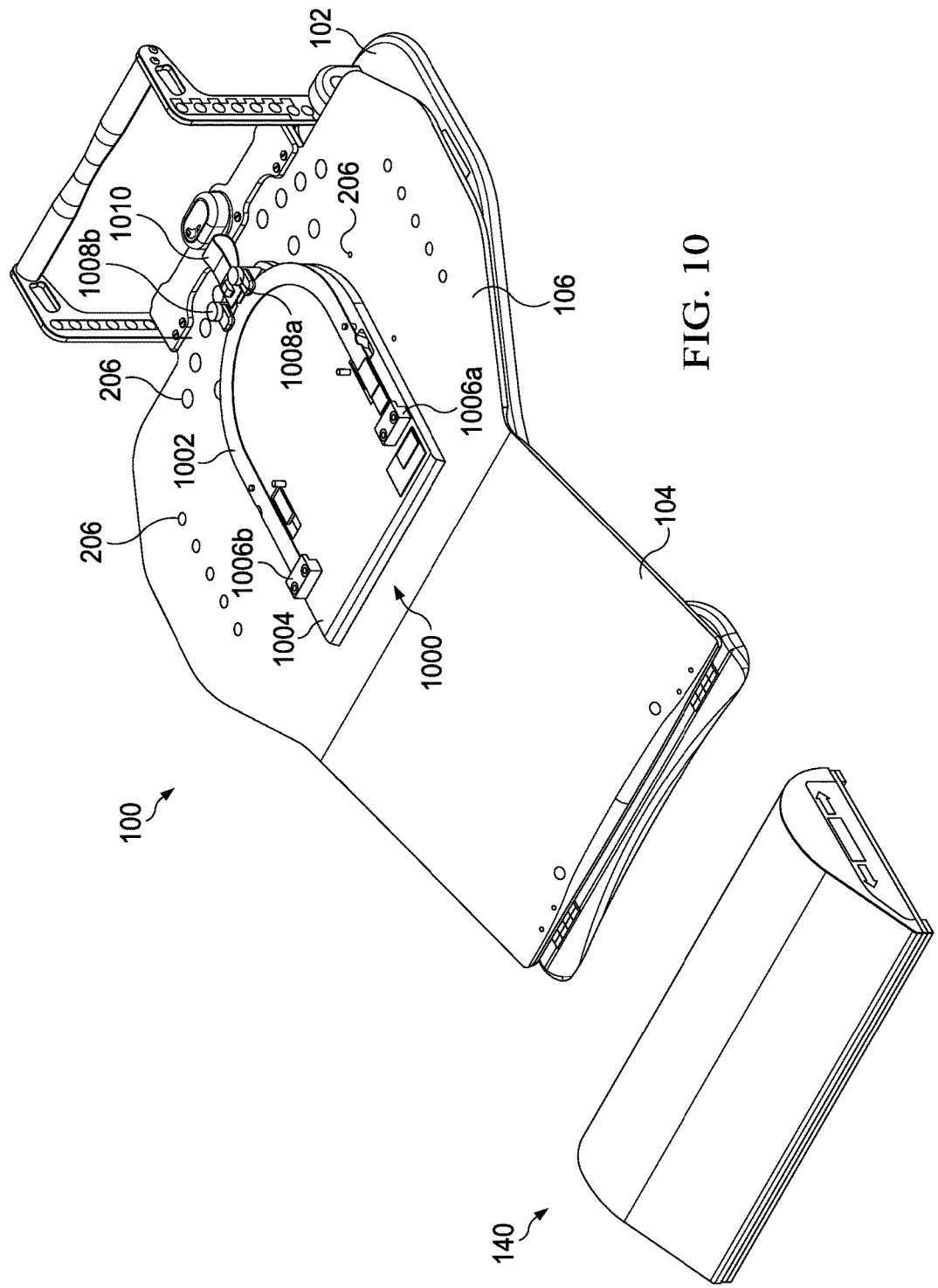
FIG. 10 illustrates an exemplary immobilization mask module coupled with an exemplary patient positioning device.

FIG. 10 illustrates an exemplary immobilization mask module 1000 according to an embodiment. Immobilization mask module 1000 may be used to couple one or more accessories, including an immobilization mask 1100 (FIG. 11), to patient positioning device 100. Immobilization mask module 1000 may comprise clip 1002, mask module base 1004, toe blocks 1006a-1006b, retainers 1008a-1008b, and safety strap 1010. Immobilization mask module 1000 and each of clip 1002, mask module base 1004, toe blocks 1006a-1006b, retainers 1008a-1008b, and safety strap 1010 may be comprised of thin and low-density materials that are low attenuating to an imaging or treatment beam.

Mask module base 1004 may comprise a carbon fiber-reinforced composite with a foam core that couples to upper patient support 106 by one or more positioning holes 204. As will be discussed in more detail below, mask module base 1004 may be constructed of any suitable materials that are radiotranslucent and/or safe for magnetic resonance imaging (MR safe).

Clip 1002 of immobilization mask module 1000 may comprise a retaining structure that couples an immobilization mask 1100 (or other accessory) to immobilization mask module 1000. Clip 1002 may comprise a U-shaped member that is shaped so that the two terminals 1200a-1200b (FIG. 12) on the first end of the clip 1002 couple with toe blocks 1006a-1006b and a center portion 1108 on the second end of the clip 1002 couple with retainers 1008a-1008b. According to an embodiment, clip 1002 comprises a thin carbon fiber-reinforced composite member that exerts sufficient force to hold an immobilization mask 1100 (or other accessory) to immobilization mask module 1000.

Figure 11:
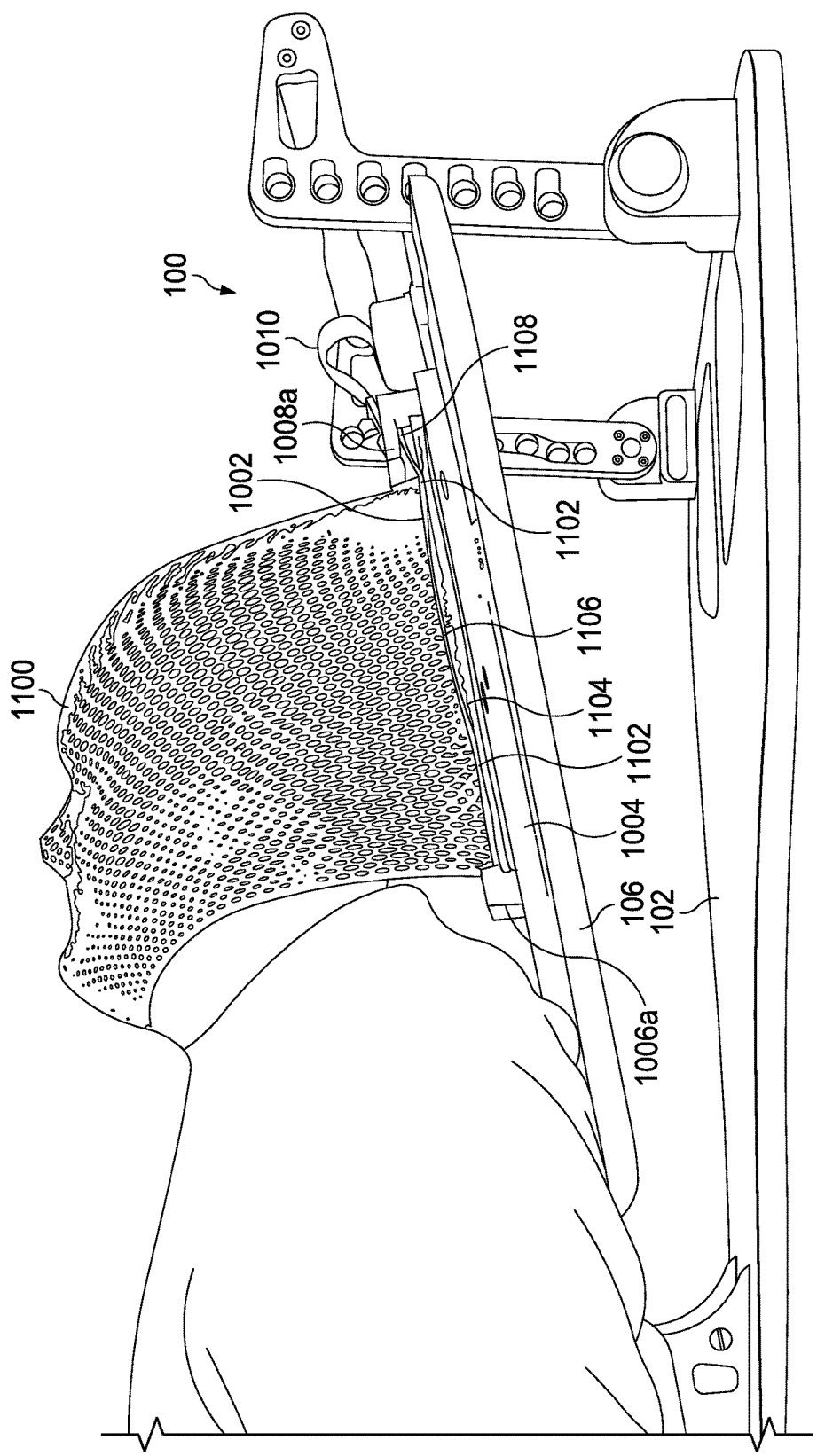
FIG. 11 illustrates an exemplary immobilization mask coupled with an exemplary patient positioning device.

FIG. 11 illustrates an exemplary immobilization mask 1100 coupled to immobilization mask module 1000 according to embodiment. Immobilization mask 1100 may comprise a rigid or semi-rigid immobilization mask 1100 that holds a patient's face in a substantially immobile position. Immobilization mask 1100 may be used for patients that cannot lie flat and may be used for head and neck cancers when those patients cannot tolerate a horizontal position due to mobility or health issues, fluid in the lungs being a common cause. Immobilization mask 1100 may couple with mask module base 1004 and may be adjusted to place patient on upper patient support 106 according to patient size and clinical requirements determined by an operator. Immobilization mask 110 may also be useful for optimizing and creating a more accurate, reproducible and immobilized head and neck position during treatment or imaging, including a more accurate chin location.

According to embodiments, immobilization mask 1100 comprises an initially pliable material that may be formed to the shape of a patient's face and then hardened (by, for example, temperature, light, or other such hardening techniques) to hold such shape. For example, immobilization mask 1100 may comprise a thermoplastic material that becomes shapeable in a hot air oven or hot water bath. After becoming shapeable, immobilization mask 1100 is formed to a patient who is reclining on patient positioning device 100 in a desired position. As the temperature cools, immobilization mask 1100 sets and/or hardens and maintains the shape of the face of the patient in the desired location. Immobilization mask 1100 may be indexed to the immobilization mask module 1000 and the upper patient support 106 (such as by positioning holes 206) and as explained in more detail below.

Immobilization mask 1100 may couple with the mask module base 1004 by clip 1002 that retains mask tab 1104. Mask tab 1104 may comprise an outer circumference of immobilization mask 1100 that is placed between clip 1002 and mask module base 1004 to hold immobilization mask 1100 securely to immobilization mask module 1000. According to an embodiment, clip 1002 comprises one or more contact points 1102 that exert pressure on mask tab 1104 that retain immobilization mask 1100 securely against mask module base 1004. Clip 1002 may additionally comprise one or more raised surfaces 1106 interposed between one or more of the contact points 1102 to provide flexion between contact points 1102 so that contact points 1102 may exert sufficient pressure on mask tab 1004 to secure mask 1100 to immobilization mask module 1000.

Figure 12:
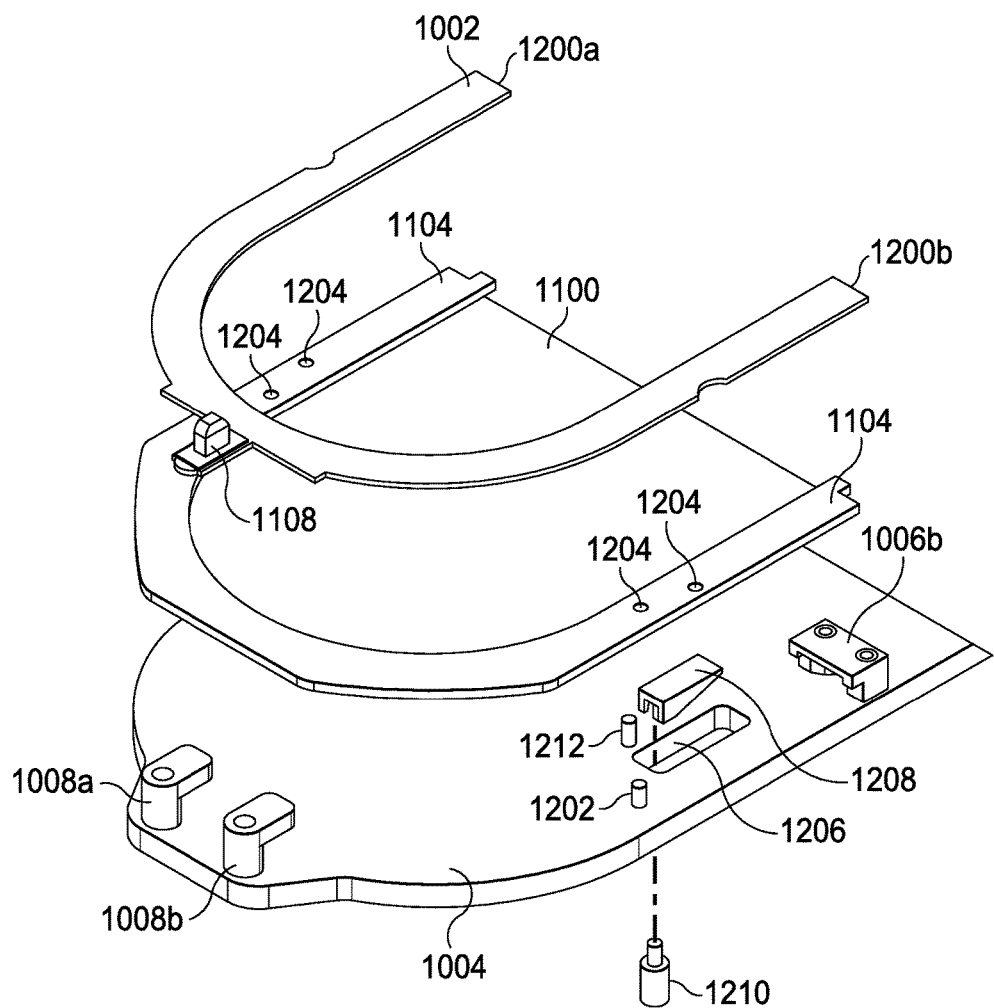
FIG. 12 illustrates an exploded view of an exemplary clip, immobilization mask, and mask module according to an embodiment.

FIG. 12 illustrates an exploded view of an exemplary clip 1002, immobilization mask 1100, and mask module 1000 according to an embodiment. Immobilization mask 1100 is illustrated in a substantially flat configuration, which illustrates how immobilization mask 1100 may appear prior to shaping to a patient's face.

Immobilization mask 1100 may be coupled and indexed to mask module 1000 by one or more mask pins 1202 of mask module base 1104. Mask pins 1202 may align and couple with mask tab holes 1204 in mask tab 1104 to secure and locate mask 1100 on mask module base 1104. This feature provides for mask 1100 to be lifted off, repositioned, and removed quickly and quietly, minimizing patient discomfort.

Figure 13B:
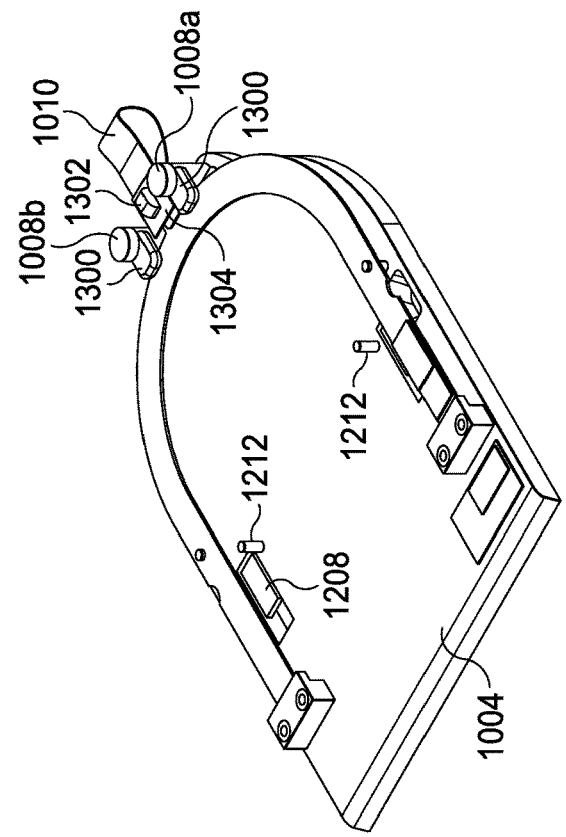
FIGS. 13A-13B illustrate an exemplary clip coupled with an exemplary immobilization mask module according to embodiments.
Figure 13A:
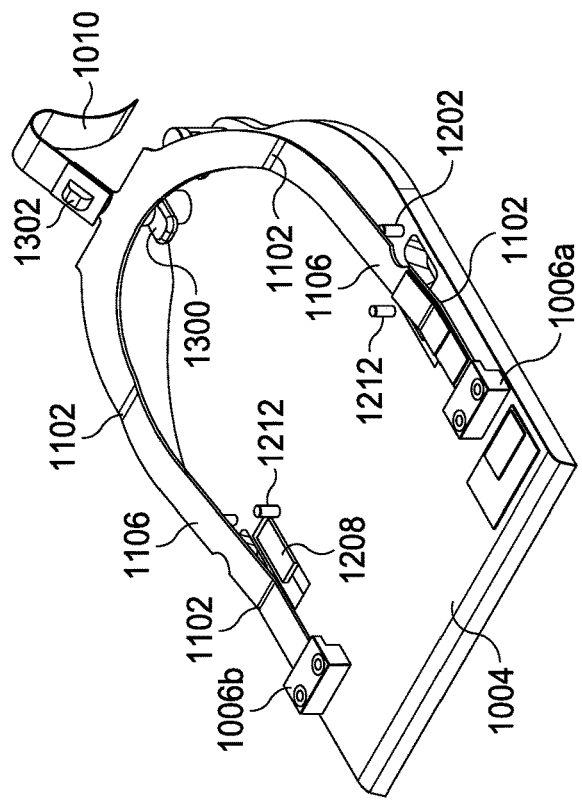

FIGS. 13A-13B illustrate an exemplary clip 1002 coupled with an exemplary immobilization mask module 1000 according to embodiments.

FIG. 13A illustrates clip 1002 comprising four contact points 1102 and two raised surfaces 1106. Although clip 1002 is illustrated with four contact points 1102 and two raised surfaces 1106, embodiments contemplate any suitable number of contact points 1102 and raised surfaces 1106 according to particular needs. To secure immobilization mask 1100 (or another accessory) to immobilization mask module 1000, mask tab 1004 may be sandwiched between clip 1002 and mask module base 1004. The two terminals 1200a-1200b on a first end of clip 1002 are secured by toe blocks 1006a-1006b, and a center portion 1108 is secured by retainers 1008a-1008b. In this manner, clip 1002 provides a spring force that holds immobilization mask 1100 (or another accessory) to mask module base 1004. Clip 1002 may couple objects as thin as a sheet of paper and at least as thick as 0.375 inches securely to the base. Clip 1002 may comprise any suitable material, such as a carbon fiber-reinforced composite, and is shaped in such a way that pressing it into retainer clips causes one or more contact points 1002 to hold an accessory securely against the base. According to some embodiments, clip 1002 may comprise KEVLAR fabric with any resin or polymer substrate, or any other suitable material. Embodiments of clip 1002 have been demonstrated to retain holding force and not wear out through many cycles. Clip 1002 is also beneficially thin and homogeneous, which eliminates extraneous structures in the board at the points where the immobilization mask 1100 couples with mask module 1000. Such structures may interfere or attenuate radiation beams.

FIG. 13B illustrates clip 1002 secured against mask module base 1004 according to an embodiment. Retainers 1008a-1008b are rotatable in relation to mask module base 1004 to which they may be coupled. As clip 1002 is pressed downward toward mask module base 1004, retainers 1008a-1008b may be rotated so that an extension 1300 is above a center portion 1108 of clip 1002. Extensions 1300 of retainers 1008a-1008b engage with center portion 1108 of clip 1002 to secure mask tab 1104 between clip 1002 and mask module base 1004. Although mask module base 1004 is illustrated with two retainers 1008a-1008b, embodiments contemplate any suitable number of retainers according to particular needs.

Safety strap 1010 may also aid in securing clip 1002 to mask module base 1004. Safety strap 1010 may comprise any suitable flexible material, such as nylon or some other fabric, that couples clip 1002 to mask module base 1004. Safety strap 1010 may provide additional security to couple clip 1002 to mask module base 1004 if one or more retainers 1008a-1008b become disengaged. Safety strap 1010 may couple to a protrusion 1302 of clip 1002 and be secured with a strap clip 1304. Safety strap 1010 may couple to clip 1002 and mask module base 1004 by, for example, hook and loop fastener, one or more clips, adhesive, or any suitable fastener.

Returning to FIG. 12, connectors for coupling mask module base 1104 to upper patient support 106 are disclosed, According to some embodiments, mask module base 1004 comprises recesses 1206. Recesses 1206 are configured to receive wedge 1208, which couples knob 1210 through mask module base 1104. Knobs 1210 may couple with positioning holes 206 in upper patient support 106. When a knob 1210 is coupled with wedge 1208 and pressure is exerted on top of wedge 1208, the bottom portion of knob 1210 expands. When knobs 1210 are coupled with positioning holes 206 and the bottom portion of knobs 1210 expands, mask module 1000 may be securely coupled to upper patient support 106. By securely coupling mask module 1000 to upper patient support 106 by knobs 1210, mask module 1000 is prevented from lifting off from upper patient support if a patient were to lift his or her head up while positioned on mask module 1000. Although wedge 1208 and knob 1210 are illustrated as coupling mask module base 1004 to upper patient support 106, embodiments contemplate wedge 1208 and knob 1210 used to fasten any suitable module or portion of patient positioning device 100. Additionally, although mask module 1000 is illustrated as securing to upper patient support 106 by knobs 1210 inserted into positioning holes 206, embodiments contemplate any suitable fasteners according to particular needs.

Mask module base 1004 may further comprise neck module pins 1212 Neck module pins 1212 may provide for coupling one or more accessories to mask module 1000, such as neck module 202. Neck module 202 may couple to mask module 1000 by neck module pins 1212 coupling with neck module holes 1400 (FIG. 14) by aligning neck module pins 1212 within neck module holes 1400. Although neck module 202 is illustrated with three pairs of neck module holes 1400 and mask module 1000 is illustrated with a single set of neck module pins 1212, embodiments contemplate any suitable number of neck module holes and neck module pins, according to particular needs. Additionally, any suitable fastener may be used to couple neck module 202 to mask module 1000 according to particular needs.

Figure 14C:
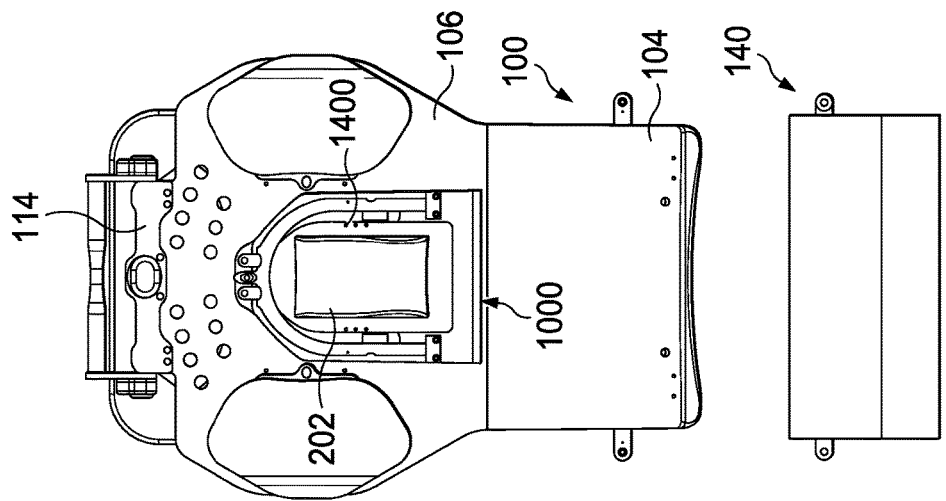
FIGS. 14A-14C illustrate a top view of an exemplary neck module coupled to an exemplary immobilization mask module according to embodiments.
Figure 14B:
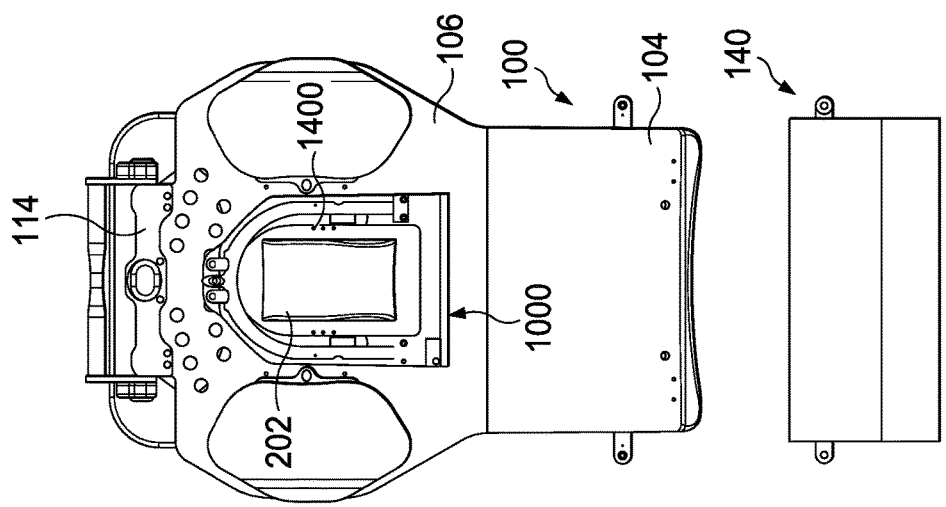
Figure 14A:
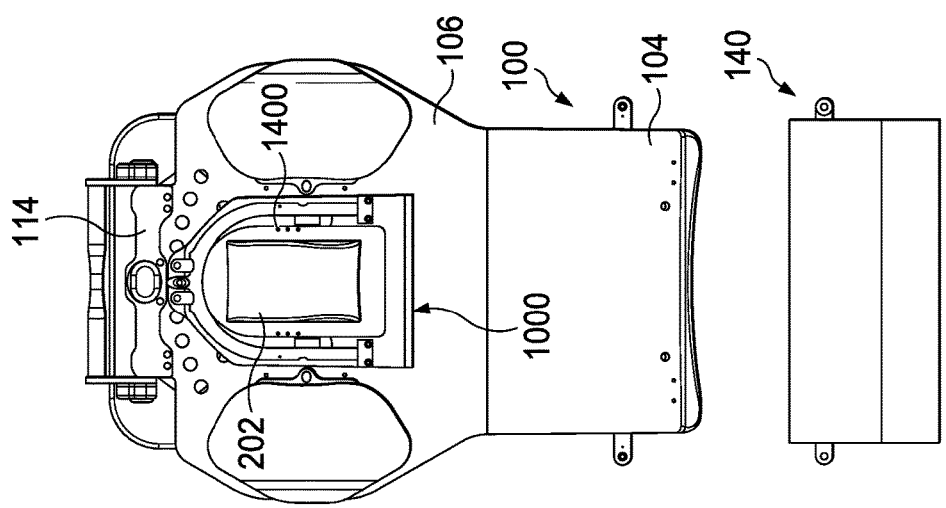

FIGS. 14A-14C illustrate a top view of an exemplary neck module 202 coupled to an exemplary immobilization mask module 1000 according to embodiments.

FIG. 14A illustrates neck module 202 coupled with immobilization mask module 1000 and patient positioning module 100 in a first position. As illustrated, neck module 202 and/or immobilization mask module 1000 may be placed in a position near upper-angle positioning module, which may place a patient's head and neck close to the forward portion of patient positioning device 100. Neck module holes 1400 may be coupled to neck module pins 1212 of immobilization mask module 1000, which is, in turn, coupled by knobs 1210 to one or more positioning holes 206 in upper patient support 106 that are nearest to upper-angle positioning module 114.

FIG. 14B illustrates neck module 202 coupled with immobilization mask module 1000 and patient positioning module 100 in a second position. As illustrated, neck module 202 and/or immobilization mask module 1000 may be placed in a position midway between upper-angle positioning module and lower patient support 104, which may place a patient's head and neck close to a middle portion of patient positioning device 100. Neck module holes 1400 may be coupled to neck module pins 1212 of immobilization mask module 1000, which is, in turn, coupled by knobs 1210 to one or more positioning holes 206 in upper patient support 106 that are midway between upper-angle positioning module 114 and lower patient support 104.

FIG. 14C illustrates neck module 202 coupled with immobilization mask module 1000 and patient positioning module 100 in a third position. As illustrated, neck module 202 and/or immobilization mask module 1000 may be placed in a position near lower patient support 104, which may place a patient's head and neck closer to the bottom portion of patient positioning device 100. Neck module holes 1400 may be coupled to neck module pins 1212 of immobilization mask module 1000, which is, in turn, coupled by knobs 1210 to one or more positioning holes 206 in upper patient support 106 that are furthest from upper-angle positioning module 114.

Although the coupling mechanisms described with respect to the patient-positioning device have been described, embodiments contemplate any suitable coupling of components such as with adhesive, a weld joint, a solder joint, a fastener (e.g. a bolt and a nut, a screw, a clip, a rivet, a pin, hook and loop fastener, and/or the like), washers, retainers, straps, wrapping, wiring, and any combination of the foregoing. Additionally, although features of the patient-positioning device are described as being separable, embodiments contemplate any feature being composed of more than one piece or multiple features being combined into a single piece, according to particular needs.

Although specific materials for each of the features of the present disclosure have been presented, embodiments contemplate various types of materials or combinations thereof that can readily be formed into shaped objects provided that the materials selected are consistent with the intended operation of the patient-positioning device. For example, the components may be formed of: rubbers (synthetic and/or natural); polymers, such as thermoplastics and thermosets; composites, such as carbon-fiber; metals; alloys; any other suitable material; and/or any combination of the foregoing.

According to embodiments, patient positioning device 100 comprises MR-safe materials, such that various materials used in the construction of patient positioning device 100 may be substituted for other optional materials. For example, according to an embodiment, screws used to fasten hinge 108 or upper-angle positioning module 114 may be made from metallic materials. According to an MR-Safe embodiment, screws may be made of non-metallic materials. Additionally, conductive materials (such as carbon fiber) may be substituted for non-conductive materials (such as Kevlar®).

Reference in the foregoing specification to "one embodiment", "an embodiment", or "another embodiment" means that a particular feature, structure, or characteristic described in connection with the embodiment is included in at least one embodiment of the invention. The appearances of the phrase "in one embodiment" in various places in the specification are not necessarily all referring to the same embodiment.

While the exemplary embodiments have been shown and described, it will be understood that various changes and modifications to the foregoing embodiments may become apparent to those skilled in the art without departing from the spirit and scope of the present invention.

What is claimed is:

1. A method of radiation therapy, comprising:
providing a radiological therapy device;
providing a patient positioning device, comprising:
a base; and
a patient support surface coupled to the base, the patient support surface comprising:
a lower patient support hingedly coupled to the base; and
an upper patient support hingedly coupled to the lower patient support;
an angle between the lower patient support and the upper patient support is adjustable by single-handed operation independently of an angle between the lower patient support and the base;
wherein the upper support surface hingedly couples to the lower patient support surface by a substantially flat hinge that forms a continuous upper surface with an upper surface of the lower patient support and an upper surface of the upper patient support;
wherein the hinge is molded at an angle greater than the angle between the lower patient support and the upper patient support when the upper patient support comprises a locked state such that the upper patient support comprises a spring action that elevates the upper patient support when the upper patient support comprises an unlocked state;
placing a patient on the patient positioning device; and
initiating the radiological therapy device.

2. The patient positioning device of claim 1, wherein the hinge comprises a fiber-reinforced composite.

3. The patient positioning device of claim 2, wherein the hinge comprises a thickness less than five millimeters.

4. The patient positioning device of claim 3, further comprising:
an upper-angle positioning module coupled to the upper patient support;
the upper-angle positioning module slideably couples with one or more armatures; and
the one or more armatures comprising one or more apertures configured to receive one or more pins of the upper-angle positioning module.

5. The patient positioning device of claim 4, wherein the one or more pins couple with the one or more armatures in a first position that anchors the upper patient support at a first angle relative to the lower patient support; and
the one or more pins couple with the one or more armatures in a second position that anchors the upper patient support at a second angle relative to the lower patient support.

6. The patient positioning device of claim 5, further comprising: an initial-angle positioning module.

7. The patient positioning device of claim 6, wherein the initial-angle positioning module comprises a wedge that removably couples with the base.

8. A patient positioning device for radiation therapy, comprising:
a base; and
a patient support coupled to the base, the patient support comprising:
a lower patient support hingedly coupled to the base;
an upper patient support hingedly coupled to the lower patient support by
an upper-angle hinge comprising a continuous upper layer that extends from a portion of the lower patient support across a flex point into a portion of the upper patient support, wherein an angle of the flex point of the upper-angle hinge when molded is greater than an angle of the flex point when the upper patient support comprises a locked state such that the upper-angle hinge comprises a spring action that elevates the upper patient support when the upper patient support comprises an unlocked state; and an upper-angle positioning module coupled to the upper patient support and providing single-handed operation to adjust the upper patient support between the locked state and the unlocked state.

9. The patient positioning device of claim 8, wherein the portion of the lower patient support and the portion of the upper patient support coupled by the upper-angle hinge are molded as a unitary component.

10. The patient positioning device of claim 9, wherein the upper-angle hinge comprises a fiber-reinforced composite.

11. The patient positioning device of claim 10, wherein the upper-angle hinge comprises filaments that extend from the portion of the lower patient support, through the flex point of the upper-angle hinge, and into the portion of the upper patient support.

12. The patient positioning device of claim 11, further comprising:
the upper-angle positioning module slideably couples with one or more armatures; and
the one or more armatures are coupled with the base and comprise one or more apertures configured to receive one or more pins of the upper-angle positioning module.

13. The patient positioning device of claim 12, wherein the one or more pins couple with the one or more armatures in a first position that anchors the upper patient support at a first angle relative to the lower patient support; and
the one or more pins couple with the one or more armatures in a second position that anchors the upper patient support at a second angle relative to the lower patient support.

14. The patient positioning device of claim 13, further comprising:
an initial-angle positioning module.

15. The patient positioning device of claim 14, wherein the initial-angle positioning module comprises a wedge that removably couples with the base.

16. A patient positioning device, comprising:
a first patient support coupled with a second patient support;
the first patient support is coupled to a base;
an angle between the first patient support and the second patient support is adjustable by single-handed operation independently of an angle between the first patient support and the base;
a hinge couples the first patient support to the second patient support and forms a continuous upper layer and extends from a portion of the first patient support into a portion of the second patient support; wherein the hinge is molded at an angle greater than the angle between the first patient support and the second patient support when the second patient support comprises a locked state such that the second patient support comprises a spring action that elevates the second patient support when the second patient support comprises an unlocked state.

17. The patient positioning device of claim 16, wherein the base couples to a treatment couch.

18. The patient positioning device of claim 17, wherein the hinge and the portion of the first patient support and the portion of the second patient support coupled by the hinge are molded as a unitary component.

19. The patient positioning device of claim 18, wherein the hinge comprises a fiber-reinforced composite.

20. The patient positioning device of claim 19, wherein the hinge comprises filaments that extend from the portion of the first patient support, through a flex point of the hinge, and into the portion of the second patient support.

21. The patient positioning device of claim 20, wherein a face immobilization module couples to one or more of the first and second patient supports.

22. The patient positioning device of claim 21, wherein a face immobilization mask couples with the face immobilization module by a U-shaped clip; and
the U-shaped clip is secured by one or more retainers and one or more toe blocks.

* * * * *